(12) United States Patent
Wang

(10) Patent No.: US 10,182,996 B2
(45) Date of Patent: Jan. 22, 2019

(54) TARGETED THERAPEUTIC NANOPARTICLES AND METHODS OF MAKING AND USING SAME

(71) Applicant: Pfizer Inc., New York, NY (US)

(72) Inventor: Hong Wang, Cambridge, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/319,458

(22) PCT Filed: Jul. 5, 2015

(86) PCT No.: PCT/US2015/038963
§ 371 (c)(1),
(2) Date: Dec. 16, 2016

(87) PCT Pub. No.: WO2016/004290
PCT Pub. Date: Jan. 7, 2016

(65) Prior Publication Data
US 2017/0128380 A1    May 11, 2017

Related U.S. Application Data

(60) Provisional application No. 62/020,609, filed on Jul. 3, 2014.

(51) Int. Cl.
*A61K 31/282* (2006.01)
*A61K 31/337* (2006.01)
*A61K 31/415* (2006.01)
*A61K 31/427* (2006.01)
*A61K 9/51* (2006.01)
*A61K 31/475* (2006.01)

(52) U.S. Cl.
CPC .......... *A61K 9/5138* (2013.01); *A61K 9/5123* (2013.01); *A61K 9/5153* (2013.01); *A61K 9/5161* (2013.01); *A61K 31/282* (2013.01); *A61K 31/337* (2013.01); *A61K 31/415* (2013.01); *A61K 31/427* (2013.01); *A61K 31/475* (2013.01)

(58) Field of Classification Search
CPC .. A61K 9/5138; A61K 9/5123; A61K 9/5153; A61K 9/5161; A61K 31/282; A61K 31/337; A61K 31/415; A61K 31/427; A61K 31/475
See application file for complete search history.

(56) References Cited

U.S. PATENT DOCUMENTS

| | | |
|---|---|---|
| 2009/0148384 A1 | 6/2009 | Fischer et al. |
| 2010/0068285 A1 | 3/2010 | Zale et al. |
| 2010/0136129 A1* | 6/2010 | Agueros Bazo ..... A61K 9/0065 424/499 |
| 2011/0250278 A1* | 10/2011 | Yuan ................... A61K 9/5138 424/490 |
| 2012/0140790 A1 | 6/2012 | Ali et al. |

FOREIGN PATENT DOCUMENTS

| | | |
|---|---|---|
| WO | 201005721 | 1/2010 |
| WO | 2012/101242 A1 * | 8/2012 |
| WO | 2013090804 | 6/2013 |

OTHER PUBLICATIONS

Evonik Technical Information for Eudragit L100 and Eudragit S100 (https://www.pharosproject.net/uploads/files/cml/1389279051.pdf, accessed Mar. 5, 2018, pp. 1-7).*
Evonik Technical Information for Eudragit E PO (Accessed Mar. 5, 2018, pp. 1-6).*
International Patent Application PCT/US2015/038963, filed Jul. 2, 2015, Search Report and Written Opinion, dated Aug. 28, 2015, 7 pages.
International Patent Application PCT/US2015/038963, filed Jul. 2, 2015, Preliminary Report on Patentability, dated Jan. 3, 2017, 6 pages.

* cited by examiner

*Primary Examiner* — Alma Pipic
(74) *Attorney, Agent, or Firm* — Richard V. Zanzalari

(57) ABSTRACT

Described herein are polymeric nanoparticles that include a therapeutic agent, and methods of making and using such therapeutic nanoparticles. In some embodiments, the contemplated nanoparticles may include an excipient.

20 Claims, 9 Drawing Sheets

TARGETED THERAPEUTIC NANOPARTICLES AND METHODS OF MAKING AND USING SAME

CROSS REFERENCE TO RELATED APPLICATIONS

This application is a national stage application under 35 U.S.C. 371 of PCT/US2015/038963, filed on Jul. 2, 2015, which claims priority to and the benefit of U.S. Provisional Patent Application No. 62/020,609, filed on Jul. 3, 2014, the entirety of which is incorporated herein by reference.

BACKGROUND

Systems that deliver certain drugs to a patient (e.g., targeted to a particular tissue or cell type or targeted to a specific diseased tissue but not normal tissue) or that control release of drugs have long been recognized as beneficial.

For example, therapeutics that include an active drug and that are, e.g., targeted to a particular tissue or cell type or targeted to a specific diseased tissue but not to normal tissue, may reduce the amount of the drug in tissues of the body that are not targeted. This is particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy. In addition, such therapeutics may allow drugs to reach certain tissues they would otherwise be unable to reach.

Therapeutics that offer controlled release and/or targeted therapy must be able to deliver an effective amount of drug, which is a known limitation in other nanoparticle delivery systems. For example, it can be a challenge to prepare nanoparticle systems that have an appropriate amount of drug associated with each nanoparticle, while keeping the size of the nanoparticles small enough to have advantageous delivery properties. However, while it is desirable to load a nanoparticle with a high quantity of therapeutic agent, nanoparticle preparations that use a drug load that is too high will result in nanoparticles that are too large for practical therapeutic use.

Accordingly, a need exists for nanoparticle therapeutics and methods of making such nanoparticles, that are capable of delivering therapeutic levels of drug to treat diseases such as cancer, while also reducing patient side effects.

SUMMARY

Described herein are polymeric nanoparticles that include a therapeutic agent, and methods of making and using such therapeutic nanoparticles. In some embodiments, the contemplated nanoparticles may include a excipient.

In one aspect, a therapeutic nanoparticle is provided. The therapeutic nanoparticle comprises about 0.05 to about 30 weight percent of an excipient selected from the group consisting of a polyanionic polymer and a polycationic polymer; about 0.2 to about 35 weight percent of a therapeutic agent; and about 35 to about 99.75 weight percent of a biocompatible polymer.

In certain embodiments, the excipient is a polyanionic polymer. For example, in certain embodiments, the polyanionic polymer is a copolymer of methacrylic acid and methyl methacrylate subunits. In some cases, the ratio of meth- acrylic acid to methyl methacrylate subunits in the polyanionic polymer is between about 1:0.9 to about 1:3.

In certain embodiments, the excipient is a polycationic polymer. For example, in certain embodiments, the polycationic polymer is a copolymer of alkyl methacrylate and dimethylaminoethylmethacrylate. In some cases, the polycationic polymer is a copolymer of dimethylaminoethyl methacrylate, butyl methacrylate, and methyl methacrylate subunits. In certain embodiments, the ratio of dimethylaminoethyl methacrylate to butyl methacrylate to methyl methacrylate subunits in the polycationic polymer is about 1:2:1.

In certain embodiments, the excipient has a molecular weight of between about 20 kDa and about 60 kDa, or between about 100 kDa and about 150 kDa.

In certain embodiments, the excipient has a glass transition temperature of between about 40° C. and about 50° C., or greater than about 100° C.

In certain embodiments, a contemplated nanoparticle comprises about 5 to about 25 weight percent of the excipient.

In certain embodiments, a contemplated nanoparticle further comprises about 0.05 to about 35 weight percent cyclodextrin, or about 15 to about 30 weight percent cyclodextrin. In some embodiments, the cyclodextrin is selected from the group consisting of α-cyclodextrin, β-cyclodextrin, γ-cyclodextrin, and mixtures thereof.

In certain embodiments, the therapeutic agent is a chemotherapeutic agent. For example, in certain embodiments the chemotherapeutic agent is selected from the group consisting of docetaxel, vincristine, vinorelbine, an epothilone, epothilone B, fluorouracil, irinotecan, capecitabine, and oxaliplatin. In certain embodiments, the therapeutic agent is a celecoxib. In certain embodiments, contemplated nanoparticles comprise about 3 to about 20 weight percent of the therapeutic agent, or about 5 to about 15 weight percent of the therapeutic agent.

In certain embodiments, the hydrodynamic diameter of a contemplated therapeutic nanoparticle is about 60 to about 200 nm, or about 90 to about 140 nm.

In certain embodiments, the biocompatible polymer is selected from the group consisting of poly(lactic) acid-poly (ethylene)glycol copolymer and poly(lactic) acid-co-poly (glycolic) acid-poly(ethylene)glycol copolymer. In certain embodiments, the poly(lactic) acid-poly(ethylene)glycol copolymer has a poly(lactic) acid number average molecular weight fraction of about 0.6 to about 0.95, about 0.6 to about 0.8, about 0.75 to about 0.85, or about 0.7 to about 0.9.

In certain embodiments, a contemplated therapeutic nanoparticle comprises about 10 to about 25 weight percent poly(ethylene)glycol, about 10 to about 20 weight percent poly(ethylene)glycol, about 15 to about 25 weight percent poly(ethylene)glycol, or about 20 to about 30 weight percent poly(ethylene)glycol.

In certain embodiments, a contemplated therapeutic nanoparticle further comprises a 1,2-distearoyl-sn-glycero-3-phosphoethanolamine-poly(ethylene)glycol copolymer.

In certain embodiments, a contemplated therapeutic nanoparticle substantially immediately releases less than about 70% of the therapeutic agent after 0.5 hours when placed in a phosphate buffer solution at 37° C.

In another aspect, a therapeutic nanoparticle is provided. The therapeutic nanoparticle is prepared by a process comprising emulsification of a first organic phase comprising a therapeutic agent or a pharmaceutically acceptable salt thereof, an excipient selected from the group consisting of a polyanionic polymer and a polycationic polymer, and a diblock poly(lactic)acid-polyethylene glycol or a diblock poly(lactic)acid-co-poly(glycolic)acid-polyethylene glycol polymer, to form an emulsion phase; quenching the emulsion phase to form a quenched phase; and filtration of the quenched phase to recover the therapeutic nanoparticle.

In yet another aspect, a pharmaceutically acceptable composition is provided. The pharmaceutically acceptable composition comprises a plurality of contemplated therapeutic nanoparticles, and a pharmaceutically acceptable excipient.

In certain embodiments, a contemplated pharmaceutically acceptable composition further comprises a saccharide and/or cyclodextrin. For example, in certain embodiments, the saccharide is a disaccharide selected from the group consisting of sucrose or trehalose, or a mixture thereof. In certain embodiments, the cyclodextrin is selected from the group consisting of α-cyclodextrin, β-cyclodextrin, γ-cyclodextrin, and mixtures thereof.

In still another aspect, a method of preparing a therapeutic nanoparticle is provided. The therapeutic nanoparticle comprises combining a therapeutic agent and a first polymer with an organic solvent to form a first organic phase having about 5 to about 50% solids; combining the first organic phase with a first aqueous solution to form a second phase, wherein the first aqueous phase comprises a non-ionic surfactant; emulsifying the second phase to form an emulsion phase; quenching the emulsion phase to form a quenched phase; and filtering the solubilized phase to recover the therapeutic nanoparticles, thereby forming a slurry of therapeutic nanoparticles having a diameter of about 80 nm to about 180 nm.

In certain embodiments, the non-ionic surfactant has a hydrophilic-lipophilic-balance (HLB) greater than about 15. For example, in certain embodiments, the non-ionic surfactant has a hydrophilic-lipophilic-balance (HLB) between about 15 and about 20. In certain embodiments, the non-ionic surfactant is a polymeric non-ionic surfactant.

In certain embodiments, the non-ionic surfactant comprises polyethylene oxide or a copolymer thereof. For example, in certain embodiments, the polymeric non-ionic surfactant is a copolymer non-ionic surfactant selected from poly(lactic acid)-polyethylene oxide copolymer and poly(lactic acid)-co-(glycolic acid)-polyethylene oxide copolymer. In certain embodiments, the copolymer non-ionic surfactant comprises polyethylene oxide having a molecular weight between about 2 kDa and about 10 kDa, or between about 4 kDa and about 6 kDa. In certain embodiments, the copolymer non-ionic surfactant comprises poly(lactic acid)-polyethylene oxide copolymer wherein the poly(lactic) acid has a molecular weight between about 0.2 kDa and about 1.0 kDa. In certain embodiments, the copolymer non-ionic surfactant comprises poly(lactic acid)-polyethylene oxide copolymer with the poly(lactic) acid having a molecular weight between about 0.4 kDa and about 0.8 kDa and the polyethylene oxide having a molecular weight between about 4 kDa and about 6 kDa.

In certain embodiments, the surfactant is a polyoxyethylene stearyl ether. For example, in certain embodiments, the polyoxyethylene stearyl ether is polyoxyethylene (100) stearyl ether. In certain embodiments, the polyoxyethylene stearyl ether has a molecular weight of between 4 kDa and 6 kDa.

In certain embodiments, the aqueous solution comprises between about 0.01 and about 5 weight percent of the surfactant, between about 0.01 and about 1 weight percent of the surfactant, between about 0.05 and about 0.2 weight percent of the surfactant, between about 1 and about 5 weight percent of the surfactant, or between about 0.01 and about 5 weight percent of the surfactant.

In certain embodiments, contemplated nanoparticles comprise about 0.2 to about 35 weight percent of the therapeutic agent, about 3 to about 35 weight percent of the therapeutic agent, or about 4 to about 15 weight percent of the therapeutic agent. In certain embodiments, the therapeutic agent is selected from the group consisting of docetaxel, vincristine, vinorelbine, an epothilone, epothilone B, fluorouracil, irinotecan, capecitabine, oxaliplatin, and celecoxib.

In certain embodiments, the first polymer comprises poly-lactic acid-polyethylene glycol diblock co-polymer. In certain embodiments, the first polymer comprises poly(lactide-co-glycolide)-poly(ethylene glycol) diblock copolymer.

In yet another aspect, a method of treating cancer in a patient in need thereof is provided. The method comprises administering to the patient a therapeutically effective amount of a composition comprising a contemplated therapeutic nanoparticle.

BRIEF DESCRIPTION OF THE DRAWINGS

FIG. 2A shows particle formation and hardening (upstream processing). FIG. 2B shows particle work up and purification (downstream processing), according to an embodiment.

DETAILED DESCRIPTION

Figure 1:
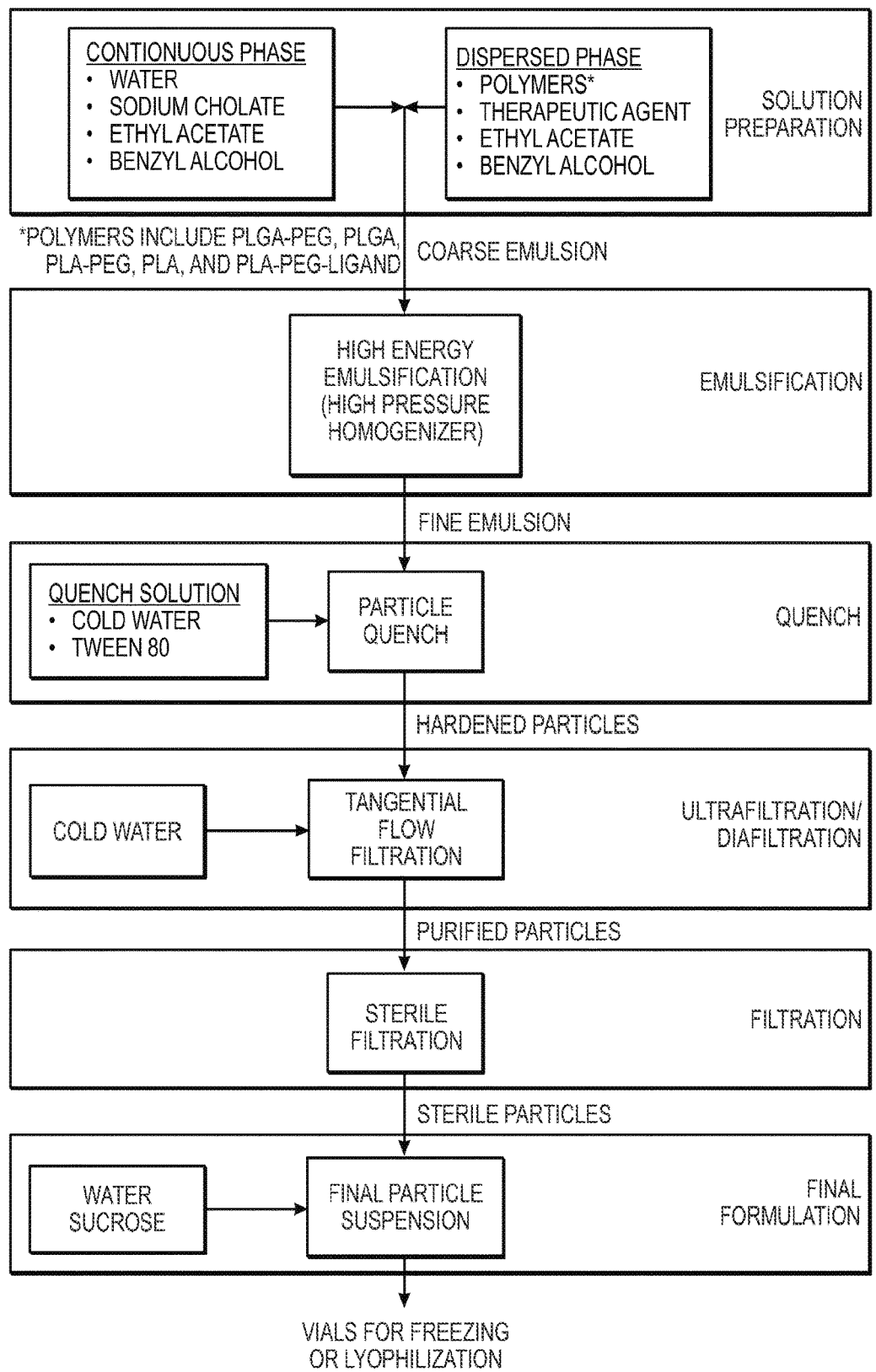
FIG. 1 is a flow chart for an emulsion process for forming disclosed nanoparticles, according to an embodiment.

Described herein are polymeric nanoparticles that include a therapeutic agent, and methods of making and using such therapeutic nanoparticles. In some embodiments, the contemplated nanoparticles may include a excipient. In some cases, including the excipient in a nanoparticle formulation enhances nanoparticle properties, such as the drug loading of the nanoparticle, as compared to nanoparticles formulated without the excipient.

Nanoparticles disclosed herein include one, two, three or more biocompatible and/or biodegradable polymers. For example, a contemplated nanoparticle may include about 35 to about 99.6 weight percent, in some embodiments about 50 to about 99.6 weight percent, in some embodiments about 50 to about 99.5 weight percent, in some embodiments about 50 to about 99 weight percent, in some embodiments about 50 to about 98 weight percent, in some embodiments about 50 to about 97 weight percent, in some embodiments about 50 to about 96 weight percent, in some embodiments about 50 to about 95 weight percent, in some embodiments about 50 to about 94 weight percent, in some embodiments about 50 to about 93 weight percent, in some embodiments about 50 to about 92 weight percent, in some embodiments about 50 to about 91 weight percent, in some embodiments about 50 to about 90 weight percent, in some embodiments about 50 to about 85 weight percent, and in some embodiments about 50 to about 80 weight percent of one or more block copolymers that include a biodegradable polymer and poly (ethylene glycol) (PEG), and about 0 to about 50 weight percent of a biodegradable homopolymer.

In some embodiments, disclosed nanoparticles may include about 0.2 to about 35 weight percent, about 0.2 to about 30 weight percent, about 0.2 to about 20 weight percent, about 0.2 to about 10 weight percent, about 0.2 to about 5 weight percent, about 0.5 to about 5 weight percent, about 0.75 to about 5 weight percent, about 1 to about 5 weight percent, about 2 to about 5 weight percent, about 3 to about 5 weight percent, about 1 to about 30 weight percent, about 1 to about 20 weight percent, about 2 to about 20 weight percent, about 5 to about 20 weight percent, about 1 to about 15 weight percent, about 2 to about 15 weight percent, about 3 to about 15 weight percent, about 4 to about 15 weight percent, about 5 to about 15 weight percent, about 1 to about 10 weight percent, about 2 to about 10 weight percent, about 3 to about 10 weight percent, about 4 to about 10 weight percent, about 5 to about 10 weight percent, about 10 to about 30 weight percent, or about 15 to about 25 weight percent of an active agent.

In some embodiments, disclosed therapeutic nanoparticles may include an excipient. An excipient may be any compound or mixture of compounds that confers an advantageous property to a nanoparticle. For example, in some embodiments, including an excipient in a nanoparticle formulation may result in increased drug loading in the nanoparticle as compared to nanoparticles formulated without the excipient. In another embodiment, the controlled release properties of a nanoparticle may be advantageously altered by use of an excipient, e.g., the release rate may be accelerated, slowed, etc. In certain embodiments, the size of the nanoparticles may be increased or decreased. In some cases, use of an excipient may allow a nanoparticle to be formulated with less of or without one or more components yet have substantially similar properties as compared to nanoparticles formulated without the excipient, including substantially similar particle size, drug loading, and/or release rate.

In some embodiments, the excipient may be a polymer. For example, in some instances, the excipient may be a polyanionic polymer or a polycationic polymer. Non-limiting examples of polyanionic and polycationic polymers include, but are not limited to, polymers and copolymers of acrylate and derivatives thereof (e.g., methacrylate and alkyl methacrylates such as methyl methacrylate, dimethylaminoethyl methacrylate, and butyl methacrylate). Non-limiting examples of polyanionic polymers include polyacrylic acid, polymethacrylic acid, Eudragit® S 100 (poly(methacrylic acid-co-methyl methacrylate) 1:2), and Eudragit® L 100 (poly(methacrylic acid-co-methyl methacrylate) 1:1)). Non-limiting examples of polycationic polymers include Eudragit® E PO (poly(butyl methacrylate-co-(2-dimethylaminoethyl) methacrylate-co-methyl methacrylate) 1:2:1).

As discussed above, in some embodiments, the excipient may be a copolymer (e.g., formed from two or more polymer subunits). In some embodiments, a copolymer formed from a first subunit and a second subunit may have a ratio of the first subunit to the second subunit of between about 5:1 to about 1:5, in some embodiments between about 4:1 to about 1:4, in some embodiments between about 3:1 to about 1:3, in some embodiments between about 2:1 to about 1:2, in some embodiments between about 1.5:1 to about 1:1.5, in some embodiments between about 2:1 to about 1:5, in some embodiments between about 1:1 to about 1:5, in some embodiments between about 1:1 to about 1:4, in some embodiments between about 1:1 to about 1:3, and in some embodiments between about 1:0.9 to about 1:3.

In some embodiments, the excipient may have a molecular weight of between about 20 kDa and about 200 kDa, in some embodiments between about 20 kDa and about 150 kDa, in some embodiments between about 20 kDa and about 125 kDa, in some embodiments between about 20 kDa and about 100 kDa, in some embodiments between about 20 kDa and about 75 kDa, in some embodiments between about 20 kDa and about 60 kDa, in some embodiments between about 40 kDa and about 60 kDa, in some embodiments between about 50 kDa and about 200 kDa, in some embodiments between about 75 kDa and about 200 kDa, in some embodiments between about 100 kDa and about 200 kDa, in some embodiments between about 125 kDa and about 200 kDa, and in some embodiments between about 100 kDa and about 150 kDa.

In some embodiments, the excipient may have a glass transition temperature of between about 30° C. and about 130° C., in some embodiments between about 30° C. and about 100° C., in some embodiments between about 30° C. and about 80° C., in some embodiments between about 30° C. and about 60° C., in some embodiments between about 35° C. and about 60° C., in some embodiments between about 40° C. and about 60° C., or in some embodiments between about 40° C. and about 50° C. In certain embodiments, the excipient may have a glass transition temperature of greater than about 40° C., in some embodiments greater than about 50° C., in some embodiments greater than about 60° C., in some embodiments greater than about 80° C., in some embodiments greater than about 100° C., in some embodiments greater than about 120° C., or in some embodiments greater than about 130° C.

In some embodiments, a nanoparticle may comprise about 0.05 to about 35 weight percent of the excipient, in some embodiments about 0.05 to about 30 weight percent of the excipient, in some embodiments about 0.1 to about 30 weight percent of the excipient, in some embodiments about 0.5 to about 30 weight percent of the excipient, in some embodiments about 1 to about 30 weight percent of the excipient, in some embodiments about 2 to about 30 weight percent of the excipient, in some embodiments about 5 to about 30 weight percent of the excipient, in some embodiments about 10 to about 30 weight percent of the excipient, in some embodiments about 15 to about 30 weight percent of the excipient, in some embodiments about 20 to about 30 weight percent of the excipient, in some embodiments about 15 to about 25 weight percent of the excipient, in some embodiments about 5 to about 25 weight percent of the excipient, in some embodiments about 5 to about 20 weight percent of the excipient, or in some embodiments about 5 to about 15 weight percent of the excipient.

In general, a "nanoparticle" refers to any particle having a diameter of less than 1000 nm, e.g., about 10 nm to about 200 nm. Disclosed therapeutic nanoparticles may include nanoparticles having a diameter of about 60 to about 200 nm, about 60 to about 190 nm, or about 70 to about 190 nm, or about 60 to about 180 nm, or about 70 to about 180 nm, or about 50 nm to about 200 nm, or about 60 to about 120 nm, or about 70 to about 120 nm, or about 80 to about 120 nm, or about 90 to about 120 nm, or about 100 to about 120 nm, or about 60 to about 130 nm, or about 70 to about 130 nm, or about 80 to about 130 nm, or about 90 to about 130 nm, or about 100 to about 130 nm, or about 110 to about 130 nm, or about 60 to about 140 nm, or about 70 to about 140 nm, or about 80 to about 140 nm, or about 90 to about 140 nm, or about 100 to about 140 nm, or about 110 to about 140 nm, or about 60 to about 150 nm, or about 70 to about 150 nm, or about 80 to about 150 nm, or about 90 to about 150 nm, or about 100 to about 150 nm, or about 110 to about 150 nm, or about 120 to about 150 nm.

Polymers

In some embodiments, the nanoparticles may comprise a matrix of polymers and a therapeutic agent. In some embodiments, a therapeutic agent and/or targeting moiety can be associated with at least part of the polymeric matrix. The therapeutic agent can be associated with the surface of, encapsulated within, surrounded by, and/or dispersed throughout the polymeric matrix.

Any suitable polymer can be used in the disclosed nanoparticles. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments include polydioxanone (PDO), polyhydroxyalkanoate, polyhydroxybutyrate, poly(glycerol sebacate), polyglycolide (i.e., poly(glycolic) acid) (PGA), polylactide (i.e., poly(lactic) acid) (PLA), poly(lactic) acid-co-poly(glycolic) acid (PLGA), polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof). In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

It is contemplated that PEG may be terminated and include an end group. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In one embodiment, the molecular weight (or e.g., the ratio of molecular weights of, e.g., different blocks of a copolymer) of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer (or e.g., the ratio of molecular weights of, e.g., different blocks of a copolymer) can be adjusted such that the particle biodegrades in the subject being treated within a reasonable period of time (ranging from a few hours to 1-2 weeks, 3-4 weeks, 5-6 weeks, 7-8 weeks, etc.).

A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary therapeutic nanoparticle that includes about 10 to about 99 weight percent poly(lactic) acid-poly(ethylene)glycol copolymer or poly(lactic)-co-poly (glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight of about 15 to about 20 kDa (e.g. 15 or 16 kDa), or about 10 to about 25 kDa of poly(lactic) acid and a number average molecular weight of about 4 to about 6 (e.g. 5 kDa), or about 2 kDa to about 10 kDa of poly(ethylene)glycol.

In some embodiments, the poly(lactic) acid-poly(ethylene)glycol copolymer may have a poly(lactic) acid number average molecular weight fraction of about 0.6 to about 0.95, in some embodiments between about 0.7 to about 0.9, in some embodiments between about 0.6 to about 0.8, in some embodiments between about 0.7 to about 0.8, in some embodiments between about 0.75 to about 0.85, in some embodiments between about 0.8 to about 0.9, and in some embodiments between about 0.85 to about 0.95. It should be understood that the poly(lactic) acid number average molecular weight fraction may be calculated by dividing the number average molecular weight of the poly(lactic) acid component of the copolymer by the sum of the number average molecular weight of the poly(lactic) acid component and the number average molecular weight of the poly(ethylene)glycol component.

Disclosed nanoparticles may optionally include about 1 to about 50 weight percent poly(lactic) acid or poly(lactic) acid-co-poly (glycolic) acid (which does not include PEG), or may optionally include about 1 to about 50 weight percent, or about 10 to about 50 weight percent or about 30 to about 50 weight percent poly(lactic) acid or poly(lactic) acid-co-poly (glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

A therapeutic nanoparticle may, in some embodiments, contain about 10 to about 30 weight percent, in some embodiments about 10 to about 25 weight percent, in some embodiments about 10 to about 20 weight percent, in some embodiments about 10 to about 15 weight percent, in some embodiments about 15 to about 20 weight percent, in some embodiments about 15 to about 25 weight percent, in some embodiments about 20 to about 25 weight percent, in some embodiments about 20 to about 30 weight percent, or in some embodiments about 25 to about 30 weight percent of poly(ethylene)glycol, where the poly(ethylene)glycol may be present as a poly(lactic) acid-poly(ethylene)glycol copolymer, poly(lactic)-co-poly (glycolic) acid-poly(ethylene) glycol copolymer, or poly(ethylene)glycol homopolymer. In certain embodiments, the polymers of the nanoparticles can be conjugated to a lipid. The polymer can be, for example, a lipid-terminated PEG. As described below, the lipid portion of the polymer can be used for self-assembly with another polymer, facilitating the formation of a nanoparticle.

For example, a hydrophilic polymer could be conjugated to a lipid that will self-assemble with a hydrophobic polymer.

In some embodiments, lipids are oils. In general, any oil known in the art can be conjugated to the polymers used in the nanoparticles. In some embodiments, an oil can comprise one or more fatty acid groups or salts thereof. In some embodiments, a fatty acid group can comprise digestible, long chain (e.g., $C_6$-$C_{50}$), substituted or unsubstituted hydrocarbons. In some embodiments, a fatty acid group can be a $C_{10}$-$C_{20}$ fatty acid or salt thereof. In some embodiments, a fatty acid group can be a $C_{15}$-$C_{20}$ fatty acid or salt thereof. In some embodiments, a fatty acid can be unsaturated. In some embodiments, a fatty acid group can be monounsaturated. In some embodiments, a fatty acid group can be polyunsaturated. In some embodiments, a double bond of an unsaturated fatty acid group can be in the cis conformation. In some embodiments, a double bond of an unsaturated fatty acid can be in the trans conformation.

In some embodiments, a fatty acid group can be one or more of butyric, caproic, caprylic, capric, lauric, myristic, palmitic, stearic, arachidic, behenic, or lignoceric acid. In some embodiments, a fatty acid group can be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In a particular embodiment, the lipid is of the Formula V:

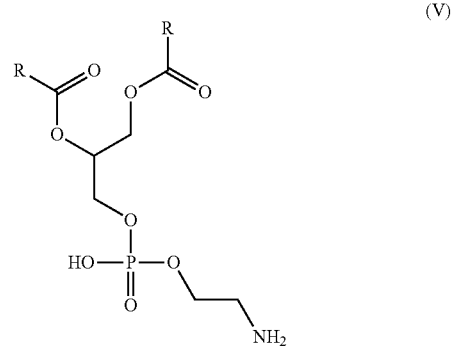

(V)

and salts thereof, wherein each R is, independently, $C_{1-30}$ alkyl. In one embodiment of Formula V, the lipid is 1,2 distearoyl-sn-glycero-3-phosphoethanolamine (DSPE), and salts thereof, e.g., the sodium salt.

In one embodiment, optional small molecule targeting moieties are bonded, e.g., covalently bonded, to the lipid component of the nanoparticle.

Nanoparticles

In one set of embodiments, the particles can have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety, may be present in both the interior and the surface of the particle, but at a higher concentration on the surface than in the interior of the particle. Although in some cases, the concentration in the interior of the particle may be essentially nonzero, i.e., there is a detectable amount of the compound present in the interior of the particle.

In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload can thus be contained within the interior of the particle, which can shelter it from the external environment surrounding the particle (or vice versa). For instance, a drug or other payload contained within a particle administered to a subject will be protected from a subject's body, and the body may also be substantially isolated from the drug for at least a period of time.

For example, disclosed herein is a therapeutic polymeric nanoparticle comprising a first non-functionalized polymer; an optional second non-functionalized polymer;

an optional functionalized polymer comprising a targeting moiety; and a therapeutic agent. In a particular embodiment, the first non-functionalized polymer is PLA, PLGA, or PEG, or copolymers thereof, e.g., a diblock co-polymer PLA-PEG. For example, exemplary nanoparticles may have a PEG corona with a density of about 0.065 g/cm$^3$, or about 0.01 to about 0.10 g/cm$^3$.

Disclosed nanoparticles may be stable (e.g., retain substantially all active agent) for example in a solution that may contain a saccharide, for at least about 3 days, about 4 days or at least about 5 days at room temperature, or at 25° C.

In some embodiments, a contemplated nanoparticle may comprise a cyclodextrin. A suitable cyclodextrin may include α-cyclodextrin, β-cyclodextrin, γ-cyclodextrin, or mixtures thereof. Exemplary cyclodextrins contemplated for use in the nanoparticles disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glucosyl-β-cyclodextrin, and maltosyl-β-cyclodextrin. In some embodiments, the cyclodextrin may be covalently attached to polymer. For example, in some embodiments, the cyclodextrin may be covalently attached to chitosan.

For example, in some embodiments, a contemplated nanoparticle may comprise about 0.05 to about 35 weight percent of a cyclodextrin, in some embodiments about 0.05 to about 30 weight percent of a cyclodextrin, in some embodiments about 0.1 to about 30 weight percent of a cyclodextrin, in some embodiments about 0.5 to about 30 weight percent of a cyclodextrin, in some embodiments about 1 to about 30 weight percent of a cyclodextrin, in some embodiments about 2 to about 30 weight percent of a cyclodextrin, in some embodiments about 5 to about 30 weight percent of a cyclodextrin, in some embodiments about 10 to about 30 weight percent of a cyclodextrin, in some embodiments about 15 to about 30 weight percent of a cyclodextrin, in some embodiments about 20 to about 30 weight percent of a cyclodextrin, in some embodiments about 15 to about 25 weight percent of a cyclodextrin, in some embodiments about 5 to about 25 weight percent of a cyclodextrin, in some embodiments about 5 to about 20 weight percent of a cyclodextrin, or in some embodiments about 5 to about 15 weight percent of a cyclodextrin.

In some embodiments, disclosed nanoparticles may also include a fatty alcohol, which may increase the rate of drug release. For example, disclosed nanoparticles may include a $C_8$-$C_{30}$ alcohol such as cetyl alcohol, octanol, stearyl alcohol, arachidyl alcohol, docosonal, or octasonal.

Nanoparticles may have controlled release properties, e.g., may be capable of delivering an amount of a therapeutic agent to a patient, e.g., to specific site in a patient, over an extended period of time, e.g., over 1 day, 1 week, or more.

In some embodiments, disclosed nanoparticles substantially immediately release (e.g., over about 1 minute to about 30 minutes) less than about 2%, less than about 4%, less than about 5%, or less than about 10% of an active agent, for example when placed in a phosphate buffer solution at room temperature and/or at 37° C.

In another embodiment, a disclosed nanoparticle may release less than about 40%, less than 50%, or less than 60%, less than 70% of an active agent for example when placed in a phosphate buffer solution at room temperature or at 37° C., for 0.5 hour or more. In one embodiment, a disclosed nanoparticle may release less than about 70% of the therapeutic agent over 0.5 hour when placed in a phosphate buffer solution at 37° C.

In another embodiment, a disclosed nanoparticle may release less than about 20%, less than about 30%, less than about 40%, less than 50%, or even less than 60% (or more) for example when placed in a phosphate buffer solution at room temperature or at 37° C., for 1 day or more. In one embodiment, a disclosed nanoparticle may release less than about 60% of the therapeutic agent over 2 hours when placed in a phosphate buffer solution at room temperature.

In some embodiments, after administration to a subject or patient of a disclosed nanoparticle or a composition that includes a disclosed nanoparticle, the peak plasma concentration ($C_{max}$) of the therapeutic agent in the patient is substantially higher as compared to a $C_{max}$ of the therapeutic agent if administered alone (e.g., not as part of a nanoparticle).

In another embodiment, a disclosed nanoparticle including a therapeutic agent, when administered to a subject, may have a $t_{max}$ of therapeutic agent substantially longer as compared to a $t_{max}$ of the therapeutic agent administered alone.

Libraries of such particles may also be formed. For example, by varying the ratios of the two (or more) polymers within the particle, these libraries can be useful for screening tests, high-throughput assays, or the like. Entities within the library may vary by properties such as those described above, and in some cases, more than one property of the particles may be varied within the library. Accordingly, one embodiment is directed to a library of nanoparticles having different ratios of polymers with differing properties. The library may include any suitable ratio(s) of the polymers.

In some embodiments, the biocompatible polymer is a hydrophobic polymer. Non-limiting examples of biocompatible polymers include polylactide, polyglycolide, and/or poly(lactide-co-glycolide).

In a different embodiment, this disclosure provides for a nanoparticle comprising 1) a polymeric matrix; 2) optionally, an amphiphilic compound or layer that surrounds or is dispersed within the polymeric matrix forming a continuous or discontinuous shell for the particle; 3) a non-functionalized polymer that may form part of the polymeric matrix, and 4) optionally, an excipient, which may form part of the polymeric matrix. For example, an amphiphilic layer may reduce water penetration into the nanoparticle, thereby enhancing drug encapsulation efficiency and slowing drug release.

As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. In some embodiments, the amphiphilic compound can be, but is not limited to, one or a plurality of the following: naturally derived lipids, surfactants, or synthesized compounds with both hydrophilic and hydrophobic moieties.

Specific examples of amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

In a particular embodiment, an amphiphilic component that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices. In addition, a mixture of lipids such as lethicin is more advantageous than one single pure lipid.

In certain embodiments a disclosed nanoparticle has an amphiphilic monolayer, meaning the layer is not a phospholipid bilayer, but exists as a single continuous or discontinuous layer around, or within, the nanoparticle. The amphiphilic layer is "associated with" the nanoparticle, meaning it is positioned in some proximity to the polymeric matrix, such as surrounding the outside of the polymeric shell, or dispersed within the polymers that make up the nanoparticle.

Preparation of Nanoparticles

Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, a polymer (e.g., copolymer, e.g., block copolymer) may be chosen for its biocompatibility and/or its ability to control immunogenicity of the resultant particle.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile, tetrahydrofuran, acetone, formamide, dimethylformamide, pyridine, dioxane, or dimethylsulfoxide may contain the polymers, and particles are formed as the water-miscible organic solution is contacted with water, a polymer nonsolvent, e.g., by pouring the water-miscible organic solution into the water at a controlled rate. The polymer contained within the water-miscible organic solution, upon contact with the polymer nonsolvent, may then precipitate to form particles such as nanoparticles.

Two liquids are said to be "immiscible" or not miscible, with each other when one is not soluble in the other to a level of at least 10% by weight at ambient temperature and pressure. Typically, an organic solution (e.g., dichloromethane, chloroform, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

In some embodiments, the aqueous solution may contain a surfactant. For example, the surfactant may be a non-ionic surfactant, an ionic surfactant, or a mixture thereof. In some instances, the non-ionic surfactant may have a hydrophilic-lipophilic-balance (HLB) greater than about 10, in some embodiments greater than about 12, in some embodiments greater than about 15, and in some embodiments greater than about 18. In some embodiments, the HLB may be between about 10 and about 20, in some embodiments between about 12 and about 20, in some embodiments between about 15 and about 20, or in some embodiments between about 18 and about 20.

In some embodiments, the non-ionic surfactant may be a polymer. For example, in some cases, the non-ionic surfactant may comprise a hydrophilic polymer, such as a polyalkylene oxide (e.g., polyethylene oxide). In some embodiments, hydrophilic polymer (e.g., polyethylene oxide) may have a molecular weight between about 2 kDa and about 10 kDa, or in some cases between about 4 kDa and about 6 kDa. In some embodiments, the non-ionic surfactant may comprise a hydrophobic polymer. For example, the hydrophobic polymer may be, in some instances, poly(lactic acid) or poly(lactic acid)-co-(glycolic acid). In some embodiments, the poly(lactic acid) or the poly(lactic acid)-co-(glycolic acid) may have a molecular weight between about 0.2 kDa and about 1.0 kDa, or in some cases between about 0.4 kDa and about 0.8 kDa. In certain embodiments, the non-ionic surfactant may be a block copolymer, e.g., polyethylene oxide-block-poly(lactic acid) or polyethylene oxide-block-poly(lactic acid)-co-(glycolic acid).

In some embodiments, the surfactant may be a polyoxyalkylene alkyl ether. For example, in some cases, the polyoxyalkylene alkyl ether may be polyoxyethylene (100) stearyl ether (i.e., Brij® 100), polyoxyethylene (20) cetyl ether (i.e., Brij® 58), or polyoxyethylene (23) lauryl ether (i.e., Brij® 35). In some embodiments, the polyoxyalkylene alkyl ether may have a molecular weight of between about 1 kDa to about 10 kDa, in some embodiments between about 1 kDa to about 8 kDa, in some embodiments between about 1 kDa to about 6 kDa, n some embodiments between about 1 kDa to about 4 kDa, n some embodiments between about 1 kDa to about 2 kDa, in some embodiments between about 2 kDa to about 10 kDa, in some embodiments between about 4 kDa to about 10 kDa, in some embodiments between about 2 kDa to about 8 kDa, in some embodiments between about 4 kDa to about 6 kDa, In certain embodiments, the aqueous solution used in formulating the contemplated nanoparticles (i.e., the aqueous phase) may comprise between about 0.01 and about 5 weight percent of the surfactant, in some embodiments between about 0.05 and about 5 weight percent of the surfactant, in some embodiments between about 0.1 and about 5 weight percent of the surfactant, in some embodiments between about 0.2 and about 5 weight percent of the surfactant, in some embodiments between about 1 and about 5 weight percent of the surfactant, in some embodiments between about 2 and about 5 weight percent of the surfactant, in some embodiments between about 0.01 and about 4 weight percent of the surfactant in some embodiments between about 0.01 and about 2 weight percent of the surfactant, in some embodiments between about 0.01 and about 1 weight percent of the surfactant, in some embodiments between about 0.01 and about 0.1 weight percent of the surfactant, in some embodiments between about 0.05 and about 2 weight percent of the surfactant, in some embodiments between about 0.05 and about 1 weight percent of the surfactant, in some embodiments between about 0.05 and about 0.2 weight percent of the surfactant, in some embodiments between about 0.1 and about 2 weight percent of the surfactant, in some embodiments between about 0.1 and about 1 weight percent of the surfactant, or in some embodiments between about 1 and about 2 weight percent of the surfactant.

Properties such as surface functionality, surface charge, size, zeta (0 potential, hydrophobicity, ability to control immunogenicity, and the like, may be highly controlled using a disclosed process. For instance, a library of particles may be synthesized, and screened to identify the particles having a particular ratio of polymers that allows the particles to have a specific density of moieties present on the surface of the particle. This allows particles having one or more specific properties to be prepared, for example, a specific size and a specific surface density of moieties, without an undue degree of effort. Accordingly, certain embodiments are directed to screening techniques using such libraries, as well as any particles identified using such libraries. In addition, identification may occur by any suitable method. For instance, the identification may be direct or indirect, or proceed quantitatively or qualitatively.

Figure 2A:
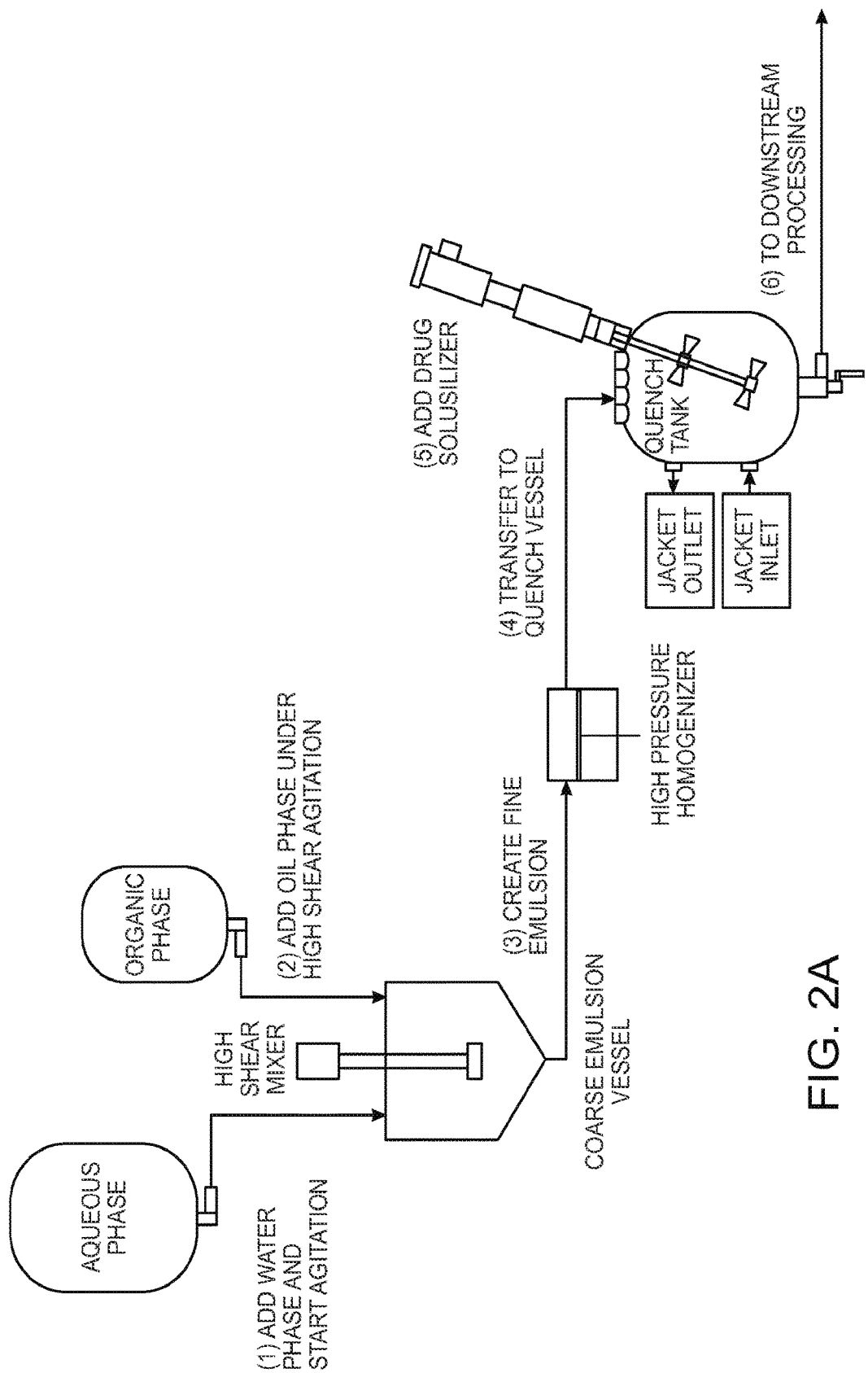
FIGS. 2A and 2B are flow diagrams for a disclosed emulsion process.
Figure 2B:
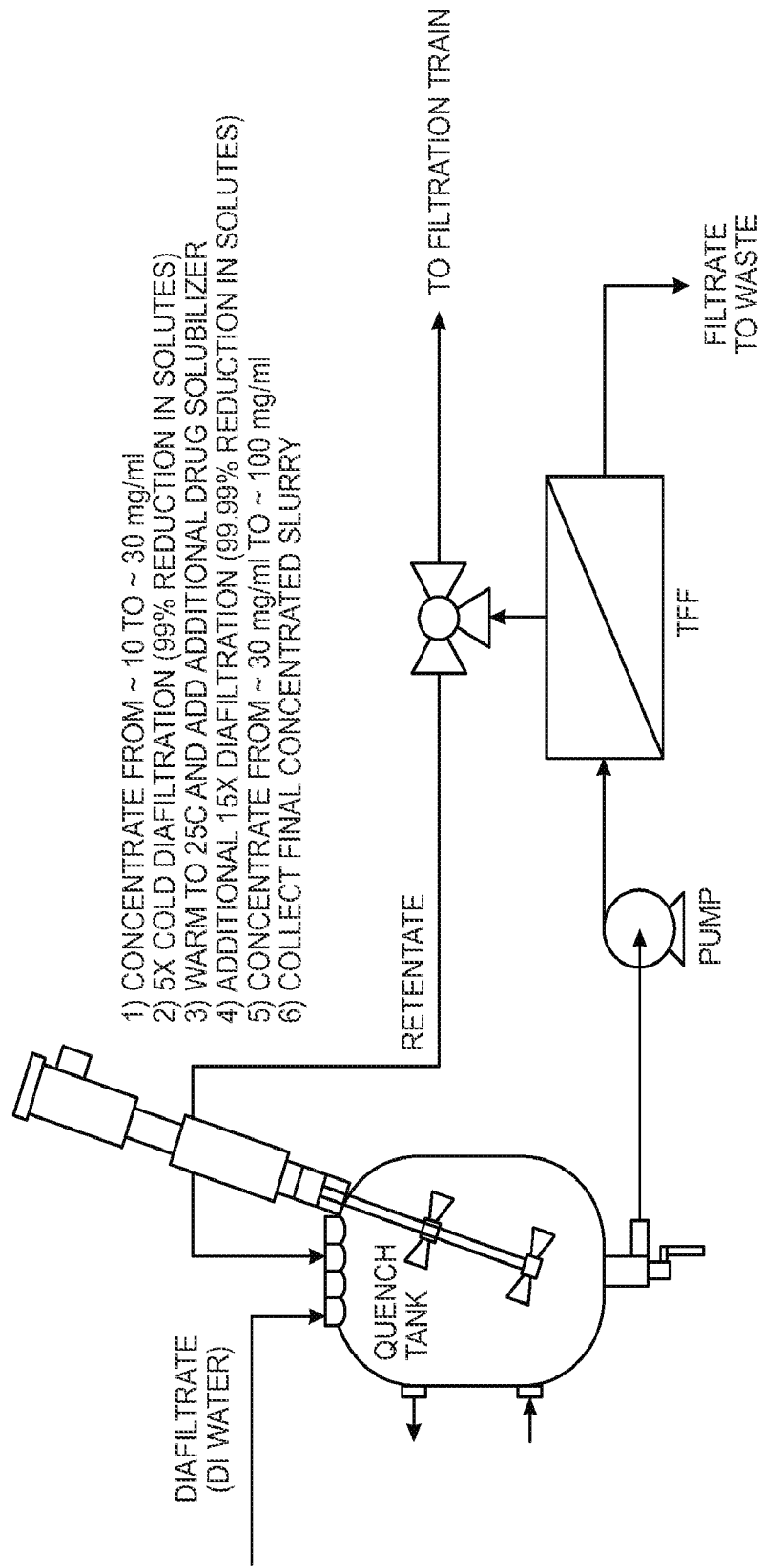

In another embodiment, a nanoemulsion process is provided, such as the process represented in FIGS. 1, 2A, and 2B. For example, a therapeutic agent, a first polymer (for example, a diblock co-polymer such as PLA-PEG or PLGA-PEG and an optional excipient (e.g., selected from the group consisting of Methacrylic Acid Copolymer, Type A—NF (i.e., Eudragit® L 100); Methacrylic Acid Copolymer, Type B—NF (i.e., Eudragit® S 100); and Amino Methacrylate Copolymer—NF (i.e., Eudragit® E PO)), may be combined with an organic solution to form a first organic phase. Such first phase may include about 1 to about 50% weight solids, about 5 to about 50% weight solids, about 5 to about 40% weight solids, about 1 to about 15% weight solids, or about 10 to about 30% weight solids. The first organic phase may be combined with a first aqueous solution, optionally including a surfactant, to form a second phase. The organic solution can include, for example, toluene, methyl ethyl ketone, acetonitrile, tetrahydrofuran, ethyl acetate, isopropyl alcohol, isopropyl acetate, dimethylformamide, dimethylsulfoxide, methylene chloride, dichloromethane, chloroform, acetone, benzyl alcohol, Tween 80, Span 80, or the like, and combinations thereof. In an embodiment, the organic phase may include benzyl alcohol, ethyl acetate, and combinations thereof. In another embodiment, the organic phase may include benzyl alcohol, ethyl acetate, dimethylformamide, dimethylsulfoxide, and combinations thereof. The second phase can be between about 0.01 and 50 weight %, 0.1 and 50 weight %, between about 1 and 50 weight %, between about 5 and 40 weight %, or between about 1 and 15 weight %, solids. The aqueous solution can be water, optionally in combination with one or more of solutes, e.g., sodium cholate, ethyl acetate, benzyl alcohol, or a surfactant selected from the group consisting of polyvinyl acetate, polyethylene oxide-block-poly(lactic acid), polyethylene oxide-block-poly(lactic acid-co-glycolic acid), and a Brij® detergent (e.g., Brij® 100, Brij® 58, and/or Brij® 35).

For example, the oil or organic phase may use a solvent that is only partially miscible with the nonsolvent (water). Therefore, when mixed at a low enough ratio and/or when using water pre-saturated with the organic solvents, the oil phase remains liquid. The oil phase may be emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate, polyethylene oxide-block-poly(lactic acid), polyethylene oxide-block-poly(lactic acid-co-glycolic acid), and/or a Brij detergent and pre-saturated with ethyl acetate and benzyl alcohol.

Emulsifying the second phase to form an emulsion phase may be performed, for example, in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer, e.g., by using 1, 2, 3, or more passes through a homogenizer. For example, when a high pressure homogenizer is used, the pressure used may be about 30 to about 60 psi, about 40 to about 50 psi, about 1000 to about 8000 psi, about 5000 to about 15000 psi, about 2000 to about 4000 psi, about 4000 to about 8000 psi, or about 4000 to about 5000 psi, e.g., about 2000, 2500, 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. In some embodiments, quenching may be performed at least partially at a temperature of about 5° C. or less. For example, water used in the quenching may be at a temperature that is less that room temperature (e.g., about 0 to about 10° C., or about 0 to about 5° C.).

In some embodiments, not all of the therapeutic agent is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, sodium cholate, diethylnitrosamine, sodium acetate, urea, glycerin, propylene glycol, glycofurol, poly(ethylene)glycol, bris(polyoxyethyleneglycolddodecyl ether, sodium benzoate, sodium salicylate, or combinations thereof. For example, Tween-80 may be added to the quenched nanoparticle suspension to solubilize the free drug (i.e., therapeutic agent) and prevent the formation of drug crystals. In some embodiments, a ratio of drug solubilizer to the therapeutic agent is about 200:1 to about 10:1, or in some embodiments about 100:1 to about 10:1.

The solubilized phase may be filtered to recover the nanoparticles. For example, ultrafiltration membranes may be used to concentrate the nanoparticle suspension and substantially eliminate organic solvent, free drug (i.e., unencapsulated therapeutic agent), drug solubilizer, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g., about 0 to about 5° C., or 0 to about 10° C.) may added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. In some embodiments, filtering may include processing about 1 to about 30, in some cases about 1 to about 15, or in some cases 1 to about 6 diavolumes. For example, filtering may include processing about 1 to about 30, or in some cases about 1 to about 6 diavolumes, at about 0 to about 5° C., and processing at least one diavolume (e.g., about 1 to about 15, about 1 to about 3, or about 1 to about 2 diavolumes) at about 20 to about 30° C. In some embodiments, filtering comprises processing different diavolumes at different distinct temperatures.

After purifying and concentrating the nanoparticle suspension, the particles may be passed through one, two or more sterilizing and/or depth filters, for example, using ~0.2 μm depth pre-filter. For example, a sterile filtration step may involve filtering the therapeutic nanoparticles using a filtration train at a controlled rate. In some embodiments, the filtration train may include a depth filter and a sterile filter.

In another embodiment of preparing nanoparticles, an organic phase is formed composed of a mixture of therapeutic agent and polymer (homopolymer and co-polymer). The organic phase is mixed with an aqueous phase at approximately a 1:5 ratio (oil phase:aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. In some embodiments, the quench:emulsion ratio may be about 2:1 to about 40:1, or in some embodiments about 5:1 to about 15:1. In some embodiments, the quench:emulsion ratio is approximately 8.5:1. Then a solution of Tween (e.g., Tween 80) is added to the quench to achieve approximately 2% Tween overall. This serves to dissolve free, unencapsulated therapeutic agent. The nanoparticles are then isolated through either centrifugation or ultrafiltration/diafiltration.

It will be appreciated that the amounts of polymer and therapeutic agent that are used in the preparation of the formulation may differ from a final formulation. For example, some of the therapeutic agent may not become completely incorporated in a nanoparticle and such free therapeutic agent may be e.g., filtered away. For example, in an embodiment, a first organic solution containing about 11 weight percent theoretical loading of therapeutic agent in a first organic solution, a second organic solution containing about 89 weight percent polymer (e.g., the polymer may include PLA-PEG), and an aqueous solution may be used in the preparation of a formulation that results in, e.g., a final nanoparticle comprising about 2 weight percent therapeutic agent and about 98 weight percent polymer (where the polymer may include PLA-PEG). Such processes may provide final nanoparticles suitable for administration to a patient that include about 1 to about 20 percent by weight therapeutic agent, e.g., about 1, about 2, about 3, about 4, about 5, about 8, about 10, or about 15 percent therapeutic agent by weight.

Therapeutic Agents

In one aspect, any agent including, for example, therapeutic agents (e.g. anti-cancer agents or anti-inflammatory agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered by the disclosed nanoparticles. Exemplary agents to be delivered in accordance with the present invention include, but are not limited to, small molecules (e.g., cytotoxic agents or anti-inflammatory agents), nucleic acids (e.g., siRNA, RNAi, and mircoRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer. In other embodiments, the agent may be useful for the treatment of an inflammatory disease.

In a particular embodiment, the drug or other payload may be released in a controlled release manner from the particle and allowed to interact locally with the particular targeting site (e.g., a tumor or inflamed tissue). The term "controlled release" (and variants of that term) as used herein (e.g., in the context of "controlled-release system") is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

The active agent or drug may be a therapeutic agent such as an antineoplastic such as mTor inhibitors (e.g., sirolimus, temsirolimus, or everolimus), *vinca* alkaloids such as vincristine, a diterpene derivative or a taxane such as paclitaxel (or its derivatives such as DHA-paclitaxel or PG-paclitaxel) or cabazitaxel.

In one set of embodiments, the payload is a drug or a combination of more than one drug. Such particles may be useful, for example, in embodiments where a targeting moiety may be used to direct a particle containing a drug to a particular localized location within a subject, e.g., to allow localized delivery of the drug to occur. Exemplary therapeutic agents include chemotherapeutic agents such as doxorubicin (Adriamycin), gemcitabine (Gemzar), daunorubicin, procarbazine, mitomycin, cytarabine, etoposide, methotrexate, venorelbine, 5-fluorouracil (5-FU), vinca alkaloids such as vinblastine or vincristine; bleomycin, paclitaxel (taxol), docetaxel (taxotere), cabazitaxel, aldesleukin, asparaginase, busulfan, carboplatin, cladribine, camptothecin, CPT-11, 10-hydroxy-7-ethylcamptothecin (SN38), dacarbazine, S-I capecitabine, ftorafur, 5'deoxyflurouridine, UFT, eniluracil, deoxycytidine, 5-azacytosine, 5-azadeoxycytosine, allopurinol, 2-chloroadenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof.

Non-limiting examples of potentially suitable drugs include anti-cancer agents, including, for example, cabazitaxel, mitoxantrone, and mitoxantrone hydrochloride. In another embodiment, the payload may be an anti-cancer drug such as 20-epi-1, 25 dihydroxyvitamin D3, 4-ipomeanol, 5-ethynyluracil, 9-dihydroxtaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizdng morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, cabazitaxel, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanospermmine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C uihibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinarnide, RNAi, rogletimide, rohitukine, romurtide, roquinimex, rubiginone Bl, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine or vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

Non-limiting examples of potentially suitable drugs also include anti-inflammatory agents, including, for example, anti-inflammatory steroids and non-steroidal anti-inflammatory agents (NSAIDs). Non-limiting examples of anti-inflammatory agents include methotrexate, cyclosporine, alclometasone, azathioprine, beclometasone dipropionate, betamethasone dipropionate, budesonide, celecoxib, chloroprednisone, ciclesonide, cortisol, cortisporin, cortivazol, deflazacort, dexamethasone, fludroxycortide, flunisolide, fluocinonide, fluocortolone, fluorometholone, fluticasone, fluticasone furoate, fluticasone propionate, glucocorticoids, hydrocortamate, megestrol acetate, mesalazine, meprednisone, 6-mercaptopurine, methylprednisolone, mometasone furoate, paramethasone, prednisolone, prednisone, prednylidene, pregnadiene, pregnatriene, pregnene, proctosedyl, rimexolone, tetrahydrocorticosterone, tobramycin/dexamethasone, triamcinolone, and ulobetasol.

Pharmaceutical Formulations

Nanoparticles disclosed herein may be combined with pharmaceutically acceptable carriers to form a pharmaceutical composition, according to another aspect. As would be appreciated by one of skill in this art, the carriers may be chosen based on the route of administration as described below, the location of the target issue, the drug being delivered, the time course of delivery of the drug, etc.

The pharmaceutical compositions can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing a therapeutic agent is chosen by the individual physician in view of the patient to be treated, in general, dosage and administration are adjusted to provide an effective amount of the therapeutic agent nanoparticle to the patient being treated. As used herein, the "effective amount" of a nanoparticle containing a therapeutic agent refers to the amount necessary to elicit the desired biological response. As will be appreciated by those of ordinary skill in this art, the effective amount of a nanoparticle containing a therapeutic agent may vary depending on such factors as the desired biological endpoint, the drug to be delivered, the target tissue, the route of administration, etc. For example, the effective amount of a nanoparticle containing a therapeutic agent might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an exemplary embodiment, a pharmaceutical composition is disclosed that includes a plurality of nanoparticles each comprising a therapeutic agent and a pharmaceutically acceptable excipient.

In an embodiment, compositions disclosed herein may include less than about 10 ppm of palladium, or less than about 8 ppm, or less than about 6 ppm of palladium. For example, provided here is a composition that includes nanoparticles wherein the composition has less than about 10 ppm of palladium.

In some embodiments, a composition suitable for freezing is contemplated, including nanoparticles disclosed herein and a solution suitable for freezing, e.g., a sugar such as a mono, di, or poly saccharide, e.g., sucrose and/or a trehalose, and/or a salt and/or a cyclodextrin solution is added to the nanoparticle suspension. The sugar (e.g., sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w) or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10-100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w).

For example, a contemplated solution may include nanoparticles as disclosed herein, about 1% to about 25% by weight of a disaccharide such as trehalose or sucrose (e.g., about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Contemplated formulations may include a plurality of disclosed nanoparticles (e.g. nanoparticles having PLA-PEG and an active agent), and about 2% to about 15 wt % (or about 4% to about 6 wt %, e.g. about 5 wt %) sucrose and about 5 wt % to about 20% (e.g. about 7% wt percent to about 12 wt %, e.g. about 10 wt %) of a cyclodextrin, e.g., HPbCD).

The present disclosure relates in part to lyophilized pharmaceutical compositions that, when reconstituted, have a minimal amount of large aggregates. Such large aggregates may have a size greater than about 0.5 μm, greater than about 1 μm, or greater than about 10 μm, and can be undesirable in a reconstituted solution. Aggregate sizes can be measured using a variety of techniques including those indicated in the U.S. Pharmacopeia at 32 <788>, hereby incorporated by reference. The tests outlined in USP 32 <788> include a light obscuration particle count test, microscopic particle count test, laser diffraction, and single particle optical sensing. In one embodiment, the particle size in a given sample is measured using laser diffraction and/or single particle optical sensing.

The USP 32 <788> by light obscuration particle count test sets forth guidelines for sampling particle sizes in a suspension. For solutions with less than or equal to 100 mL, the preparation complies with the test if the average number of particles present does not exceed 6000 per container that are ≥10 µm and 600 per container that are ≥25 µm.

As outlined in USP 32 <788>, the microscopic particle count test sets forth guidelines for determining particle amounts using a binocular microscope adjusted to 100±10× magnification having an ocular micrometer. An ocular micrometer is a circular diameter graticule that consists of a circle divided into quadrants with black reference circles denoting 10 µm and 25 µm when viewed at 100× magnification. A linear scale is provided below the graticule. The number of particles with reference to 10 µm and 25 µm are visually tallied. For solutions with less than or equal to 100 mL, the preparation complies with the test if the average number of particles present does not exceed 3000 per container that are ≥10 µm and 300 per container that are ≥25 µm.

In some embodiments, a 10 mL aqueous sample of a disclosed composition upon reconstitution comprises less than 600 particles per ml having a size greater than or equal to 10 microns; and/or less than 60 particles per ml having a size greater than or equal to 25 microns.

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 µm. By knowing the particle concentration of the measured sample, the weight percentage of aggregates or the aggregate concentration (particles/mL) can be calculated.

Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β,β-trehalose, α,β-trehalose, sophorose, laminaribiose, gentiobiose, turanose, maltulose, palatinose, gentiobiulose, mannobiase, melibiose, melibiulose, rutinose, rutinulose, and xylobiose. Reconstitution shows equivalent DLS size distributions when compared to the starting suspension. However, laser diffraction can detect particles of >10 µm in size in some reconstituted solutions. Further, SPOS also may detect >10 µm sized particles at a concentration above that of the FDA guidelines ($10^4$-$10^5$ particles/mL for >10 µm particles).

In some embodiments, one or more ionic halide salts may be used as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. In one embodiment, the lyophilized pharmaceutical composition may comprise about 10 to about 100 mM sodium chloride. In another embodiment, the lyophilized pharmaceutical composition may comprise about 100 to about 500 mM of divalent ionic chloride salt, such as calcium chloride or zinc chloride. In yet another embodiment, the suspension to be lyophilized may further comprise a cyclodextrin, for example, about 1 to about 25 weight percent of cyclodextrin may be used.

A suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glucosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG, an active/therapeutic agent, about 4% to about 6% (e.g. about 5% wt percent) sucrose, and about 8 to about 12 weight percent (e.g. about 10 wt. %) HPbCD.

In one aspect, a lyophilized pharmaceutical composition is provided comprising disclosed nanoparticles, wherein upon reconstitution of the lyophilized pharmaceutical composition at a nanoparticle concentration of about 50 mg/mL, in less than or about 100 mL of an aqueous medium, the reconstituted composition suitable for parenteral administration comprises less than 6000, such as less than 3000, microparticles of greater than or equal to 10 microns; and/or less than 600, such as less than 300, microparticles of greater than or equal to 25 microns.

The number of microparticles can be determined by means such as the USP 32 <788> by light obscuration particle count test, the USP 32 <788> by microscopic particle count test, laser diffraction, and single particle optical sensing.

In an aspect, a pharmaceutical composition suitable for parenteral use upon reconstitution is provided comprising a plurality of therapeutic particles each comprising a copolymer having a hydrophobic polymer segment and a hydrophilic polymer segment; an active agent; a sugar; and a cyclodextrin.

For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

The step of adding a disaccharide and an ionic halide salt may comprise adding about 5 to about 15 weight percent sucrose or about 5 to about 20 weight percent trehalose (e.g., about 10 to about 20 weight percent trehalose), and about 10 to about 500 mM ionic halide salt. The ionic halide salt may be selected from sodium chloride, calcium chloride, and zinc chloride, or mixtures thereof. In an embodiment, about 1 to about 25 weight percent cyclodextrin is also added.

In another embodiment, the step of adding a disaccharide and a cyclodextrin may comprise adding about 5 to about 15 weight percent sucrose or about 5 to about 20 weight percent trehalose (e.g., about 10 to about 20 weight percent trehalose), and about 1 to about 25 weight percent cyclodextrin. In an embodiment, about 10 to about 15 weight percent cyclodextrin is added. The cyclodextrin may be selected from α-cyclodextrin, β-cyclodextrin, γ-cyclodextrin, or mixtures thereof.

In another aspect, a method of preventing substantial aggregation of particles in a pharmaceutical nanoparticle composition is provided comprising adding a sugar and a salt to the lyophilized formulation to prevent aggregation of the nanoparticles upon reconstitution. In an embodiment, a cyclodextrin is also added to the lyophilized formulation. In yet another aspect, a method of preventing substantial aggregation of particles in a pharmaceutical nanoparticle composition is provided comprising adding a sugar and a cyclodextrin to the lyophilized formulation to prevent aggregation of the nanoparticles upon reconstitution.

A contemplated lyophilized composition may have a therapeutic particle concentration of greater than about 40 mg/mL. The formulation suitable for parenteral administration may have less than about 600 particles having a size greater than 10 microns in a 10 mL dose. Lyophilizing may comprise freezing the composition at a temperature of greater than about −40° C., or e.g. less than about −30° C., forming a frozen composition; and drying the frozen composition to form the lyophilized composition. The step of drying may occur at about 50 mTorr at a temperature of about −25 to about −34° C., or about −30 to about −34° C.

In an embodiment, provided herein is a pharmaceutical aqueous suspension comprising a plurality of nanoparticles, for example, as disclosed herein, having a glass transition temperature between about 37° C. and about 50° C., or about 37° C. and about 39° C. in said suspension.

Methods of Treatment

In some embodiments, contemplated nanoparticles may be used to treat, alleviate, ameliorate, relieve, delay onset of, inhibit progression of, reduce severity of, and/or reduce incidence of one or more symptoms or features of a disease, disorder, and/or condition. In some embodiments, contemplated nanoparticles may be used to treat solid tumors, e.g., cancer and/or cancer cells.

The term "cancer" includes pre-malignant as well as malignant cancers. Cancers include, but are not limited to, blood (e.g., leukemia, chronic myelogenous leukemia, chronic myelomonocytic leukemia, acute lymphoblastic leukemia, Philadelphia chromosome positive acute lymphoblastic leukemia, mantle cell lymphoma, non-Hodgkin's lymphoma, Hodgkin's lymphoma), prostate, gastric cancer, colorectal cancer, skin cancer, e.g., melanomas or basal cell carcinomas, lung cancer (e.g., non-small cell lung cancer), breast cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer (e.g., hepatocellular carcinoma), kidney cancer (e.g., renal cell carcinoma, acute nephroblastoma), testicular cancer, biliary tract cancer, small bowel or appendix cancer, gastrointestinal stromal tumor, salivary gland cancer, thyroid gland cancer, adrenal gland cancer, osteosarcoma, chondrosarcoma, cancer of hematological tissues, and the like. "Cancer cells" can be in the form of a tumor (i.e., a solid tumor), exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect, a method for the treatment of cancer is provided. In some embodiments, the treatment of cancer comprises administering a therapeutically effective amount of inventive particles to a subject in need thereof, in such amounts and for such time as is necessary to achieve the desired result. In certain embodiments, a "therapeutically effective amount" of a contemplated nanoparticle is that amount effective for treating, alleviating, ameliorating, relieving, delaying onset of, inhibiting progression of, reducing severity of, and/or reducing incidence of one or more symptoms or features of cancer.

In one aspect, a method for administering inventive compositions to a subject suffering from cancer is provided. In some embodiments, particles may be administered to a subject in such amounts and for such time as is necessary to achieve the desired result (i.e., treatment of cancer). In certain embodiments, a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of an inventive targeted particle to a healthy individual (i.e., a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, disclosed nanoparticles can be used to inhibit the growth of cancer cells, e.g., lung or colon cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Also provided herein are methods of administering to a patient a nanoparticle disclosed herein including an active agent, wherein, upon administration to a patient, such nanoparticles substantially reduces the volume of distribution and/or substantially reduces free $C_{max}$, as compared to administration of the agent alone (i.e., not as a disclosed nanoparticle).

Also provided herein are methods of treating an inflammatory disease in a patient in need thereof. The method comprises administering to the patient a therapeutically effective amount of the inventive nanoparticles. In some embodiments, the inflammatory disease may be inflammatory bowel disease, such as Crohn's disease, ulcerative colitis, collagenous colitis, lymphocytic colitis, ischemic colitis, diversion colitis, Behçet's disease, or indeterminate colitis. In other embodiments, a method of treating irritable bowel syndrome in a patient in need thereof is provided. The method comprises administering to the patient a therapeutically effective amount of inventive nanoparticles. In some embodiments, the nanoparticles may contain a therapeutic agent. For example, in certain embodiments, the therapeutic agent may be an anti-inflammatory agent, such as described above.

EXAMPLES

The invention now being generally described, it will be more readily understood by reference to the following examples which are included merely for purposes of illustration of certain aspects and embodiments, and are not intended to limit the invention in any way.

Example 1

Patupilone Nanoparticle Formulations Containing a Eudragit Excipient

Therapeutic nanoparticles were produced using the following formulation:
25% (w/w) theoretical drug;
75% (w/w) Polymer (80% 16/5 PLA-PEG (16 kDa PLA, 5 kDa PEG) and 20% Eudragit polymer);
% Total Solids=10%; and
Solvents: 20% benzyl alcohol/water (92.5% benzyl alcohol, 7.5% water (w/w)), 80% ethyl acetate (w/w).
For a 1 gram batch size, 125 mg of drug were dissolved in benzyl alcohol containing 7.5 wt. % water to form a drug solution. 16/5 PLA-PEG (300 mg) was dissolved in ethyl acetate to form a PLA-PEG solution. Eudragit polymer (75 mg) was dissolved in either drug solution or PLA-PEG solution. Drug solution and polymer solution were mixed immediately before formulation of the nanoparticles.

Therapeutic nanoparticles are produced as follows. In order to prepare a drug/polymer solution, 125 mg of patupilone were added to a 20 mL glass vial along with 900 mg of benzyl alcohol containing 7.5% water. The mixture was vortexed until the drug was mostly dissolved, thereby forming the drug solution. To a second 20 mL glass vial was added 300 mg of 16/5 PLA-PEG and 3.6 g of ethyl acetate. The mixture was vortexed until the PLA-PEG was mostly dissolved, thereby forming the polymer solution. Eudragit (75 mg) was added to either the drug solution or the polymer solution and vortexed until most of the Eudragit was dissolved. The polymer solution was then poured into the drug solution and vortexed until a clear solution was observed.

An aqueous solution was prepared containing 0.1% Brij 100 dissolved in a solution of 4% benzyl alcohol in water (w/w). Specifically, a 5% Brij 100 solution containing 4% benzyl alcohol was prepared by mixing 227.5 g water, 10 g benzyl alcohol, and 12.5 g Brij 100 in a 500 mL glass bottle on a stir plate until all of the components were dissolved, thereby forming a concentrated aqueous solution. The concentrated aqueous solution was then cooled to less than 5° C. A diluent composed of 4% benzyl alcohol in water was prepared by mixing 80 g of benzyl alcohol and 1920 g of water in a 500 mL glass bottle on a stir plate until dissolved. The diluent was then cooled to less than 5° C. The aqueous solution was then prepared by adding 10 g of the concentrated aqueous solution to 490 g of diluent and mixing on a stir plate.

An emulsion was formed by combining the organic phase into the aqueous solution at a ratio of 5:1 (aqueous phase:oil phase). The organic phase was poured into the aqueous solution and homogenized using a hand homogenizer for 15 seconds at room temperature to form a coarse emulsion. The coarse emulsion was subsequently fed through a high pressure homogenizer (110S) by setting the pressure to 45 psi for one pass to form a nanoemulsion.

The nanoemulsion was quenched into cold DI water at <5° C. while stirring on a stir plate. The ratio of Quench to Emulsion was 10:1. 35% (w/w) Tween 80 in water was then added to the quenched emulsion at a ratio of 150:1 (Tween 80:drug).

The nanoparticles were concentrated through tangential flow filtration (TFF) followed by diafiltration to remove solvents, unencapsulated drug, and solubilizer. A quenched emulsion was initially concentrated through TFF using a 300 KDa Pall cassette (3 membrane) to an approximately 200 mL volume. This was followed by diafiltration using approximately 20 diavolumes (4 L) of cold DI water. The volume was minimized by adding 100 mL of cold water to the vessel and pumping through the membrane for rinsing. Approximately 60 mL of material were collected in a glass vial.

In order to determine the solids concentration of unfiltered final slurry, a 10 mL volume of final slurry was added to a tared 20 mL scintillation vial and dried under vacuum on lyo/oven. Subsequently, the weight of nanoparticles was determined in the volume of the dried down slurry. Concentrated sucrose (0.666 g/g) is added to the final slurry sample to attain a final concentration of 10% sucrose.

In order to determine the solids concentration of 0.45 μm filtered final slurry, a portion of the final slurry sample is filtered before the addition of sucrose using a 0.45 μm syringe filter. A volume of the filtered sample is then added to a tared 20 mL scintillation vial and dried under vacuum on lyo/oven. The remaining sample of unfiltered final slurry is frozen with sucrose.

Three Eudragit formulations of Patupilone, lots 281-8-1, 281-80-1R, and 281-8-2, were made of under different emulsification conditions as listed in Table 1 below. Lot 186-101-8 was made without Eudragit polymer under comparable conditions.

The data in Table 1 show drug load and particle size for all formulations. Compared to nanoparticles (NPs) prepared without using Eudragit, the drug loading of Eudragit NPs showed an increase of more than threefold, up to 15.18%.

TABLE 1

| 16/5 PLA-PEG Lot # | Eudragit excipient | Drug theoretical loading (%) | Solid conc | Loading % | size (nm) | Notes |
|---|---|---|---|---|---|---|
| 186-101-8 | No | 15 | 15% | 2.92 | 83.8 | 0.01% Docusate, 1pass at 10485 psi |
| 281-8-1 | Eudragit L100, 20% of polymer | 25 | 10% | 11.57% | 145.1 | 0.1% Brij, 1pass at 46 psi |
| 281-8-1R | Eudragit EPO, 20% of polymer | 25 | 10% | 11.70% | 117.2 | 0.1% Brij, 1pass at 46 psi |
| 281-8-2 | Eudragit S100, 20% of polymer | 25 | 10% | 15.18% | 125.8 | 0.14% Brij, 2passes at 46 psi |

Figure 3:
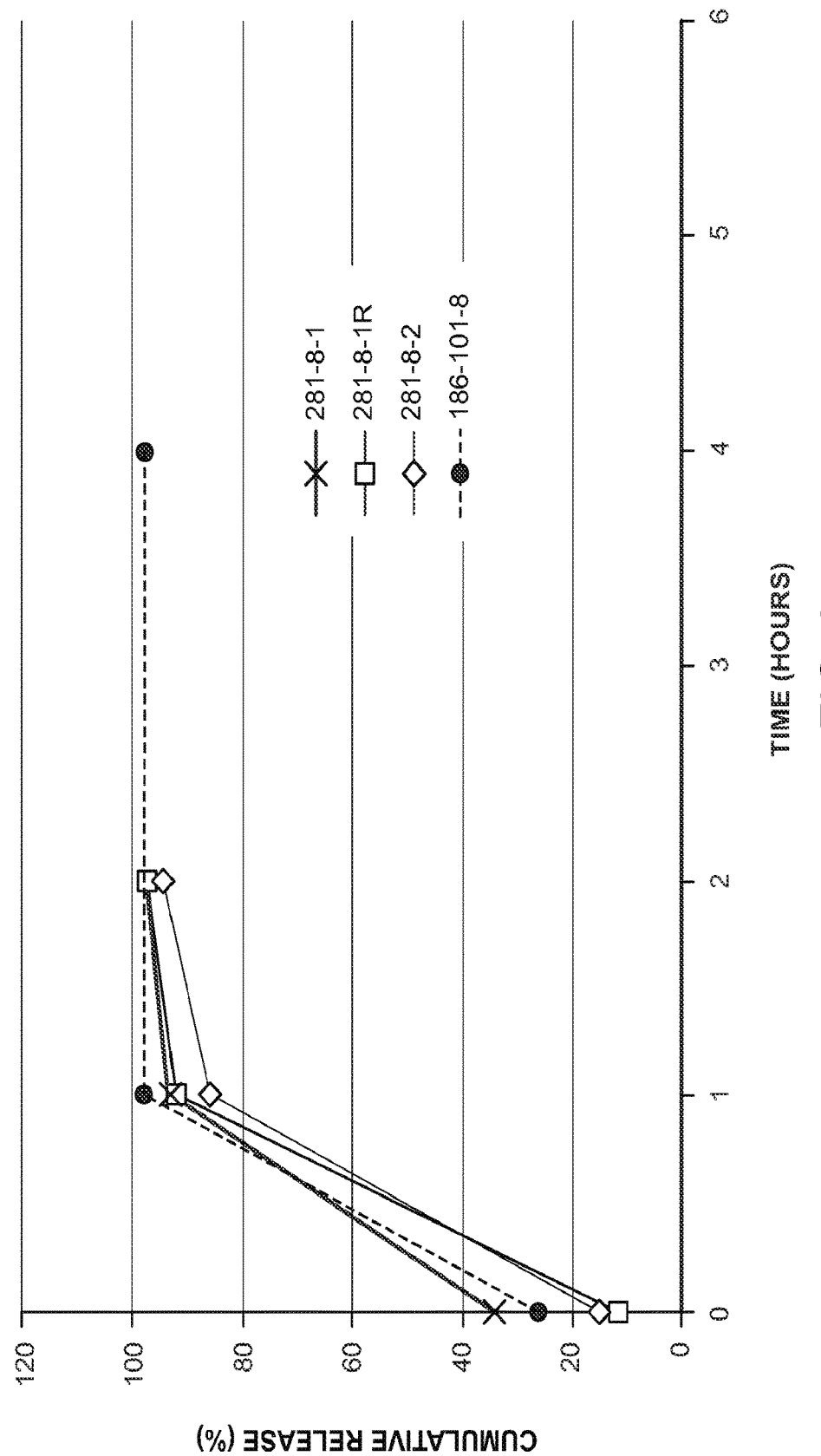
FIG. 3 shows in vitro release data for contemplated patupilone nanoparticle formulations containing a Eudragit excipient as compared to a control.

FIG. 3 shows in vitro release data for the formulations of Table 1. Nearly 100% of the patupilone was released from the NPs after one hour regardless of whether or not the formulation contained Eudragit. Additionally, the Eudragit excipient in the NPs did not change in vitro release profiles.

Example 2

Docetaxel Nanoparticle Formulations Containing a Eudragit Excipient

Nanoparticles containing docetaxel were prepared similarly as described above in Example 1. Table 2 shows NP properties and release rates for docetaxel nanoparticles.

TABLE 2

Impact of Eudragit, hydrophobic CD, and combination of Eudragit/CD on in vitro release of docetaxel (DTXL) from 16/5 PLA-PEG NPs.

| Lot# | Excipient | Load-ing | Size (nm) | In vitro release as a function of time (% docetaxel) | | | | |
|---|---|---|---|---|---|---|---|---|
| | | | | 0 h | 1 h | 2 h | 4 h | 24 h |
| 287-07-5 | Control: DTXL | 8.66 | 134 | 15 | 50 | 61 | 71 | 96 |
| 287-07-3 | DTXL: 10% Eudragit S100 | 9.15 | 134 | 9 | 28 | 34 | 40 | 55 |
| 284-30-3 | DTXL: 18% Eudragit S100 | 9.23 | 134 | 13 | 28 | 33 | 36 | 51 |
| 287-38-2 | DTXL: 28% Eudragit S100 | 8.10 | 135 | 43 | 62 | 66 | 72 | 92 |
| 287-07-1 | DTXL: 10% Eudragit S100, 25% CD | 8.59 | 137 | 6 | 15 | 17 | 20 | 27 |
| 287-07-4 | DTXL: 25% CD | 7.56 | 139 | 7 | 22 | 26 | 30 | 41 |
| 284-30-2 | DTXL: 32% CD | 7.14 | 125 | 6 | 15 | 18 | 21 | 29 |

Figure 4:
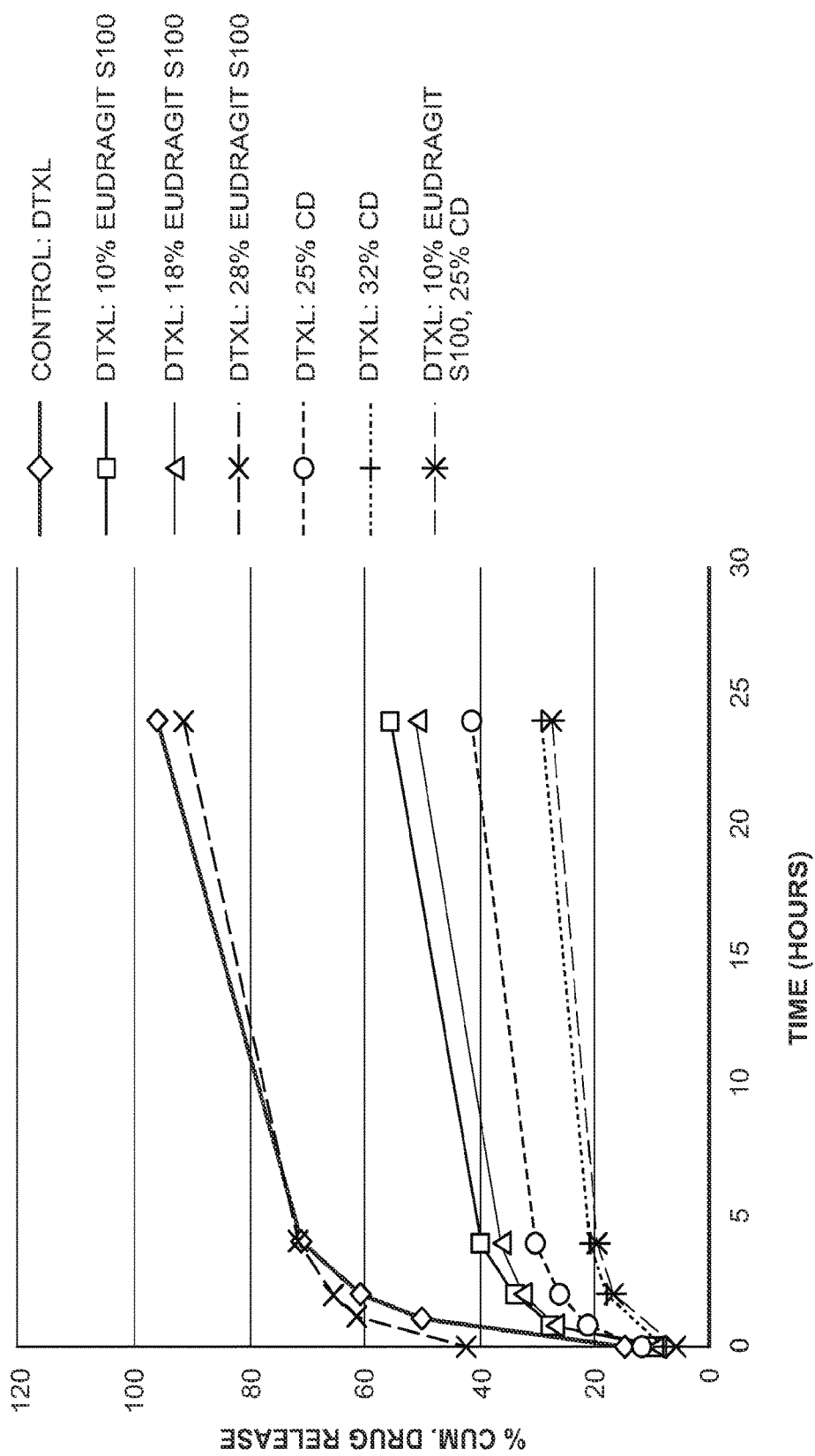
FIG. 4 shows in vitro release data for contemplated docetaxel nanoparticle formulations containing a Eudragit excipient and/or cyclodextrin as compared to a control.

FIG. 4 shows in vitro release data for the formulations of Table 2. Addition of Eudragit, CD, or the combination of Eudragit and CD slowed down the release of docetaxel in comparison to polymer alone. One exception was the addition of 28% Eudragit, which showed similar release to polymer alone. Formulations containing 10% or 18% Eudragit had similar release profiles. Increasing the amount of CD from 25% to 32% slowed release. The combination of 10% Eudragit/25% CD showed a similar release profile as 32% CD alone. The addition of Eudragit, CD, or the combination of both impacts docetaxel in vitro release. In all cases, it slowed down the release with the exception of the addition of 28% Eudragit, as noted above.

Example 3

Celecoxib Nanoparticle Formulations Containing a Eudragit Excipient

Nanoparticles containing celecoxib were prepared similarly as described above in Example 1. Table 3 shows NP properties and release rates for celecoxib nanoparticles.

TABLE 3

Impact of Eudragit, hydrophobic CD, and combination of Eudragit/CD on in vitro release of celecoxib from 50/5 PLA-PEG NPs.

| Lot# | Excipient | Load-ing | Size (nm) | In vitro release as a function of time (% docetaxel) | | | |
|---|---|---|---|---|---|---|---|
| | | | | 0 h | 1 h | 2 h | 4 h |
| 118-86-8 | Control: 50/5 PLA-PEG | 18.3 | 133 | 25.4 | 96.0 | 99.4 | 98.3 |
| 118-151-1 | Control: 50/5 PLA-PEG | 3.48 | 146.2 | 20.6 | 79.0 | 89.1 | 95.7 |
| 287-20-3 | Celecoxib: 10% Eudragit S100 | 8.72 | 154 | 29.1 | 88.0 | 94.4 | 98.7 |
| 287-20-1 | Celecoxib: 10% Eudragit S100, 25% CD | 7.77 | 186 | 21.8 | 59.0 | 64.7 | 75.6 |
| 287-20-5 | Celecoxib: 10% Eudragit S100, 25% CD | 2.38 | 137 | 33.7 | 74.4 | 79.5 | 79.0 |

TABLE 3-continued

Impact of Eudragit, hydrophobic CD, and combination of Eudragit/CD on in vitro release of celecoxib from 50/5 PLA-PEG NPs.

| Lot# | Excipient | Load-ing | Size (nm) | In vitro release as a function of time (% docetaxel) | | | |
|---|---|---|---|---|---|---|---|
| | | | | 0 h | 1 h | 2 h | 4 h |
| 287-20-7 | Celecoxib: 19% CD | 7.14 | 112 | 26.1 | 83.9 | 89.6 | 94.4 |
| 284-52-2 | Celecoxib: 19% CD | 10.54 | 221 | 18.0 | 78.1 | 84.0 | 87.6 |
| 287-20-4 | Celecoxib: 25% CD | 7.53 | 119 | 28.9 | 81.5 | 84.3 | 92.9 |
| 284-52-1 | Celecoxib: 25% CD | 11.23 | 228 | 19.5 | 70.5 | 78.0 | 84.5 |
| 287-20-6 | Celecoxib: 29% CD | 6.81 | 120 | 26.1 | 74.6 | 81.5 | 86.0 |

Figure 5:
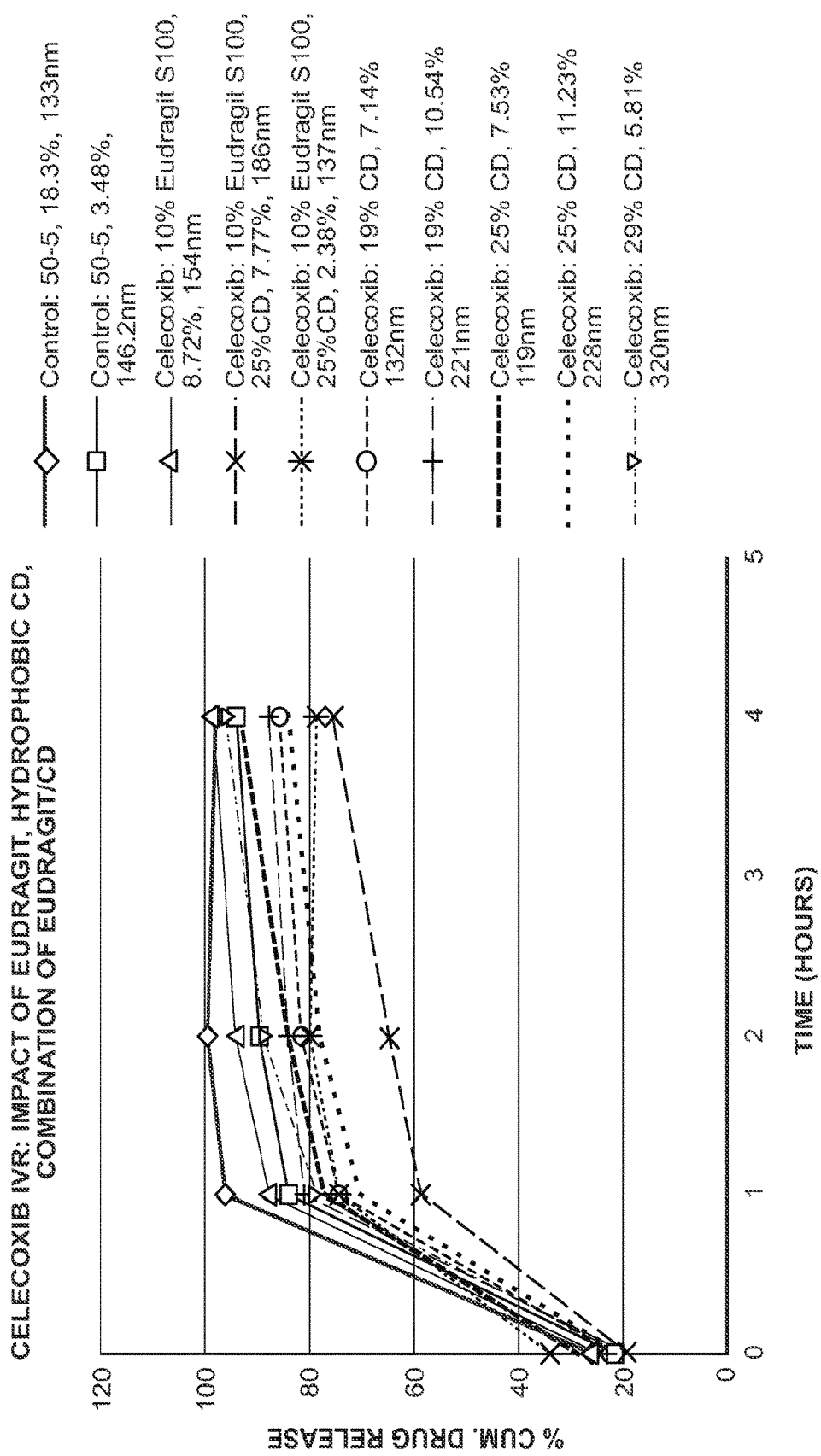
FIG. 5 shows in vitro release data for contemplated celecoxib nanoparticle formulations containing a Eudragit excipient and/or cyclodextrin as compared to controls.

FIG. 5 shows in vitro release data for the formulations of Table 3. The formulations released between approximately 75-96% of the celecoxib after 1 hour with the exception of the 287-20-1 formulation (186 nm particle), which released approximately 60% of the celecoxib after 1 hour.

Example 4

Docetaxel Nanoparticle Formulations Containing a PEO-PLA Excipient

Therapeutic nanoparticles were produced using the following formulation:
20% (w/w) theoretical drug;
80% (w/w) Polymer (16/5 PLA-PEG);
% Total Solids=20%;
Solvents: 21% benzyl alcohol, 79% ethyl acetate (w/w);
Surfactant in aqueous phase: PEO(5 kDa)-block-PLA(0.5 kDa), PEO(5 kDa)-block-PLA(0.6 kDa), or sodium cholate.

For a 0.5 gram batch size (lots 150-155-1 and 150-155-2), 100 mg of drug 400 mg of 16/5 PLA-PEG were used. For a 1 gram batch size (lots 150-173-2 and 150-173-3), 200 mg of drug and 800 mg of 16/5 PLA-PEG were used.

Therapeutic nanoparticles are produced as follows. In order to prepare a drug/polymer solution, 100 mg of docetaxel and 400 mg of polymer were added to a 7 mL glass vial along with 2000 mg of benzyl alcohol/ethyl acetate mixture (21 wt. %/79 wt. %, respectively). The mixture was vortexed until the drug and polymer were dissolved.

An aqueous solution was prepared containing 0.1% PEO-PLA dissolved in a solution of 2 wt. % benzyl alcohol and 4 wt. % ethyl acetate in water. Specifically, to a 250 mL bottle was added 0.1 g PEO-PLA and 93.9 g of DI water and the mixture stirred on a stir plate until dissolved. To this solution was added 2 g of benzyl alcohol and 4 g of ethyl acetate and the mixture stirred on a stir plate until dissolved.

An emulsion was formed by combining the organic phase into the aqueous solution at a ratio of 5:1 (aqueous phase:oil phase). The organic phase was poured into the aqueous solution and homogenized using a hand homogenizer for 10 seconds at room temperature to form a coarse emulsion. The coarse emulsion was subsequently fed through a high pressure homogenizer (110S) by setting the pressure to 45 psi for one pass to form a nanoemulsion.

The nanoemulsion was quenched into cold DI water at <5° C. while stirring on a stir plate. The ratio of Quench to Emulsion was 5:1.

The nanoparticles were concentrated through tangential flow filtration (TFF) followed by diafiltration to remove solvents, unencapsulated drug, and solubilizer. A quenched emulsion was initially concentrated through TFF using a 300 KDa Pall cassette (2 membrane) to an approximately 200 mL volume. This was followed by diafiltration using approximately 20 diavolumes (4 L) of cold DI water. The volume was minimized by adding 100 mL of cold water to the vessel and pumping through the membrane for rinsing. Approximately 50-100 mL of material were collected in a glass vial.

In order to determine the solids concentration of unfiltered final slurry, a 10 mL volume of final slurry was added to a tared 20 mL scintillation vial and dried under vacuum at 80° C. in a vacuum oven. Subsequently, the weight of nanoparticles was determined in the volume of the dried down slurry. Concentrated sucrose (0.111 g/g) is added to the final slurry sample to attain a final concentration of 10% sucrose.

In order to determine the solids concentration of 0.45 µm filtered final slurry, a portion of the final slurry sample is filtered before the addition of sucrose using a 0.45 µm syringe filter. A volume of the filtered sample is then added to a tared 20 mL scintillation vial and dried at 80° C. in a vacuum oven. The remaining sample of unfiltered final slurry is frozen with sucrose.

Figure 6:
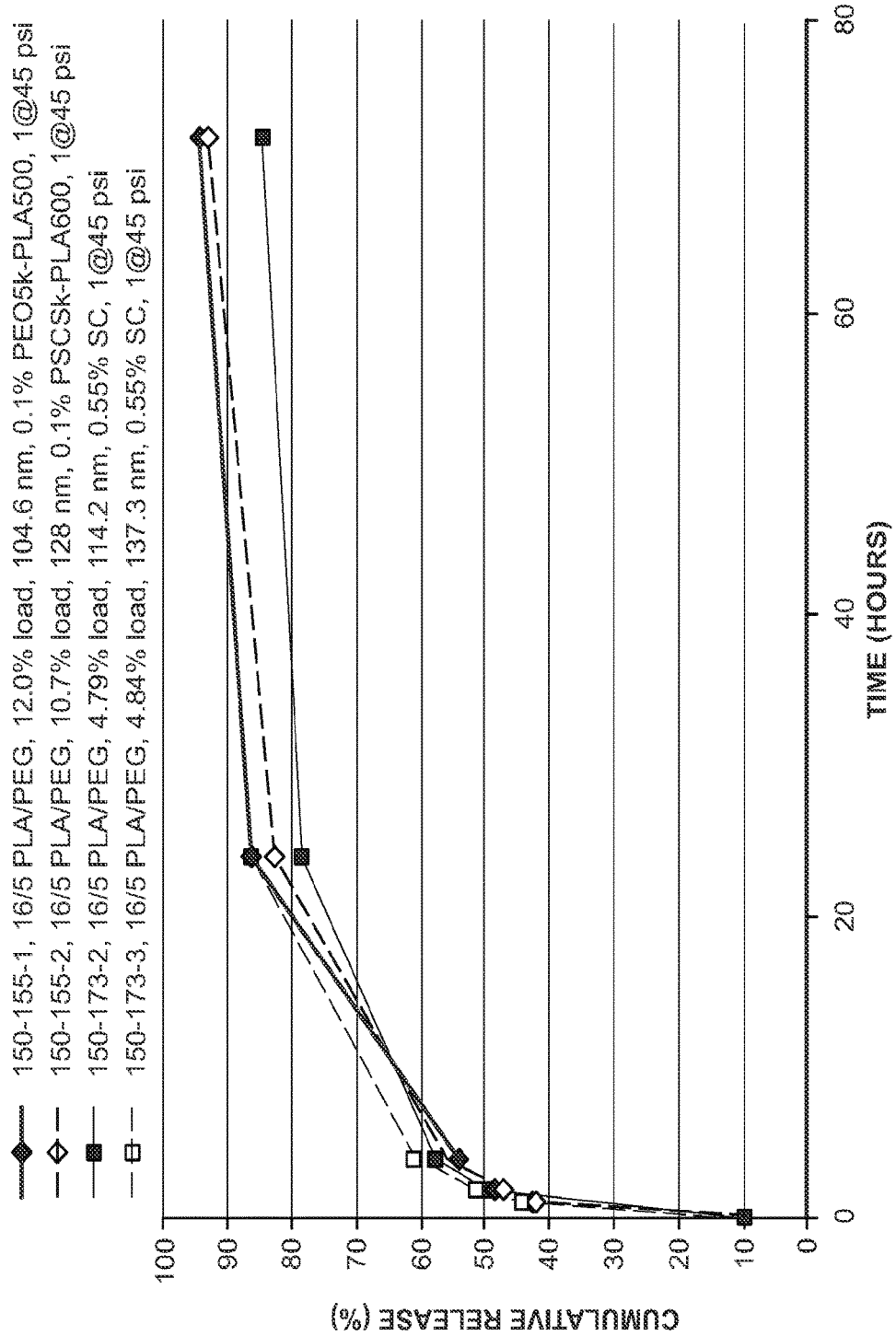
FIG. 6 shows in vitro release data for contemplated docetaxel nanoparticle formulations containing a polyethylene oxide-polylactic acid block copolymer (PEO-PEG) excipient as compared to controls.

Table 4 shows the conditions used for formulation nanoparticles. Table 5 shows certain properties of the nanoparticles. Table 6 shows the results of in vitro release of docetaxel from the nanoparticles. FIG. 6 also shows the in vitro release properties of nanoparticles prepared using PEO-PLA versus SC.

TABLE 4

Formulation conditions.

| Lot # | PLA-PEG | Drug | Drug theoretical loading % | Solid conc. | Surfactant | pass# @ psi# |
|---|---|---|---|---|---|---|
| 150-155-1 | 16/5 | Docetaxel | 20 | 20% | 0.1% PEO5k-PLA500 | 1@45 psi |
| 150-155-2 | 16/5 | Docetaxel | 20 | 20% | 0.1% PEO5k-PLA600 | 1@45 psi |
| 150-155-5 | 16/5 | Docetaxel | 20 | 20% | 0.65% SC | 1@45 psi |
| 150-173-2 | 16/5 | Docetaxel | 20 | 20% | 0.55% SC | 1@45 psi |
| 150-173-3 | 16/5 | Docetaxel | 20 | 20% | 0.525% SC | 1@45 psi |

TABLE 5

Nanoparticle properties.

| Lot # | Loading % | size (nm) | NP Solids (mg/mL) | Glass transition temperature (Tg, ° C.) |
|---|---|---|---|---|
| 150-155-1 | 9.39% | 104.6 | 4.475 | 42.2 |
| 150-155-2 | 10.71% | 128 | 5.00 | 40.03 |
| 150-155-5 | 3.54% | 86.5 | 3.575 | 41.73 |
| 150-173-2 | 4.79% | 114.2 | 7.425 | NA |
| 150-173-3 | 4.84% | 137.1 | 6.05 | NA |

TABLE 6

| | Cumulative in vitro release (%). | | | |
|---|---|---|---|---|
| Time (hours) | 150-155-1 | 150-155-2 | 150-173-2 | 150-173-3 |
| 0 | 9.74 | 17.99 | 11.31 | 12.36 |
| 1 | 40.88 | 43.00 | 42.86 | 45.58 |
| 2 | 46.68 | 48.50 | 49.94 | 51.28 |
| 4 | 55.09 | 55.72 | 57.59 | 61.25 |
| 24 | 85.73 | 82.95 | 78.59 | 86.24 |
| 72 | 94.28 | 93.30 | 84.68 | 92.60 |

PEO-PLA block polymers used as surfactants in this study are composed of a long PEG chain and a short PLA chain. Because the high hydrophilic-lipophilic balance (HLB) value, ~18, this type of polymer is water soluble and could be used to stabilize an oil/water (O/W) emulsion. For a nanoemulsion method using PLA-PEG polymer to formulate nanoparticles, this type of surfactant can be advantageous, for example, in terms of pharmaceutical acceptance for residual surfactant, because PEO-PLA has essentially the same components as PLA-PEG.

Four formulations were prepared using PEO5 k-PLA0.5 k or PEO5 k-PLA0.6 k as surfactant (150-155-1, 150-155-2, 150-155-3, and 150-155-4). Two formulations were also prepared as controls using sodium cholate surfactant (150-155-5 and 150-155-6). Stable emulsions were formed for all formulations.

For 16/5 PLA-PEG, 9.39% to 10.71% docetaxel was loaded in nanoparticles using 0.1% of PEO5 k-PLA0.5 k (150-155-1) or PEO5 k-PLA0.6 k (150-155-2) solution as the aqueous phase, with particle sizes of 104.6 nm and 128 nm, respectively.

For 47/5 PLA-PEG (i.e., 47 kDa PLA-5 kDa PEG), 14.46% to 16.29% docetaxel was loaded in nanoparticles using 1.37% of PEO5 k-PLA0.5 k (150-155-3) or 1.17% of PEO5 k-PLA0.6 k (150-155-4) solution as the aqueous phase, with particle sizes of 208.2 nm and 251.1 nm, respectively. These particles could be optimized by using higher concentration PEO-PLA aqueous solution.

Comparing to corresponding control, 150-155-1 and 150-155-2 versus 150-155-5, and 150-155-3 and 150-155-4 versus 150-155-6, the NPs prepared using PEO-PLA as surfactant have significantly higher drug loadings than those using sodium cholate as surfactant.

Collected nanoparticle solids concentrations were comparable to controls despite the PEO-PLA lots being prepared on a 0.5-gram scale and the sodium cholate (SC) lots being prepared on a 1-gram scale. The lowest solids concentration for 150-155-3, 1.75 mg/mL, was due to a large collection volume, which diluted the final NP concentration.

The glass transition temperatures of all PEO-PLA lots were higher or close to those of NPs using sodium cholate as surfactant and were well above 37° C.

In vitro release profiles of all listed lots using SC or PEGylated PLA surfactants were similar, with cumulative release of about 10-20% at T=0, about 40-45% at T=1 hour, about 45-50% at T=2 hours, and about 55-60% at T=4 hours.

Overall, no significant difference was observed for particles produced using PEO-PLA or sodium cholate as surfactant with respect to drug loading, yield, particle size, and in vitro release. PEO-PLA as surfactant yields equivalent or improved nanoparticles as compared to sodium cholate.

Additionally, much lower PEO-PLA concentrations (0.1% and <2%) were used as compared to SC (0.65% and 5%). Inclusion of PEO-PLA in a nanoparticle formulation may be advantageous when formulating nanoparticles from high molecular weight PLA-PEG polymers, which, in some cases, benefit from surfactants with higher emulsification capability to produce nanoparticles having smaller diameters.

Further benefits to using PEO-PLA over sodium cholate are (1) same type of polymer as PLA-PEG, which is well-accepted as an injectable pharmaceutical component, (2) non-ionic neutral molecule, which is inert to most compounds, (3) lower concentration than sodium cholate when making nanoparticles under the same conditions, which potentially broadens formulation capability.

Example 5

Docetaxel Nanoparticle Formulations Containing a Brij 100 Excipient

Therapeutic nanoparticles were produced using the following formulation:
20% (w/w) theoretical drug;
80% (w/w) Polymer (16/5 PLA-PEG or 47/5 PLA-PEG);
% Total Solids=20%;
Solvents: 21% benzyl alcohol, 79% ethyl acetate (w/w);
Surfactant in aqueous phase: Brij 100, or sodium cholate.
For a 1 gram batch size, 200 mg of drug and 800 mg of 16/5 PLA-PEG or 47/5 PLA-PEG were used.

Therapeutic nanoparticles are produced as follows. In order to prepare a drug/polymer solution, 200 mg of docetaxel and 800 mg of polymer were added to a 20 mL glass vial along with 4000 mg of benzyl alcohol/ethyl acetate mixture (21 wt. %/79 wt. %, respectively). The mixture was vortexed until the drug and polymer were dissolved.

An aqueous solution was prepared containing 0.1% Brij 100 dissolved in a solution of 2 wt. % benzyl alcohol and 4 wt. % ethyl acetate in water. Specifically, to a 1 L bottle was added 1 g Brij 100 and 939 g of DI water and the mixture stirred on a stir plate until dissolved. To this solution was added 20 g of benzyl alcohol and 40 g of ethyl acetate and the mixture stirred on a stir plate until dissolved.

An emulsion was formed by combining the organic phase into the aqueous solution at a ratio of 5:1 (aqueous phase:oil phase). The organic phase was poured into the aqueous solution and homogenized using a hand homogenizer for 10 seconds at room temperature to form a coarse emulsion. The coarse emulsion was subsequently fed through a high pressure homogenizer (110S) by setting the pressure to 45 psi for one pass to form a nanoemulsion.

The nanoemulsion was quenched into cold DI water at <5° C. while stirring on a stir plate. The ratio of Quench to Emulsion was 5:1.

The nanoparticles were concentrated through tangential flow filtration (TFF) followed by diafiltration to remove solvents, unencapsulated drug, and solubilizer. A quenched emulsion was initially concentrated through TFF using a 300 KDa Pall cassette (2 membrane) to an approximately 200 mL volume. This was followed by diafiltration using approximately 20 diavolumes (4 L) of cold DI water. The volume was minimized by adding 100 mL of cold water to the vessel and pumping through the membrane for rinsing. Approximately 50-100 mL of material were collected in a glass vial.

In order to determine the solids concentration of unfiltered final slurry, a 10 mL volume of final slurry was added to a tared 20 mL scintillation vial and dried under vacuum at 80° C. in a vacuum oven. Subsequently, the weight of nanoparticles was determined in the volume of the dried down slurry. Concentrated sucrose (0.111 g/g) is added to the final slurry sample to attain a final concentration of 10% sucrose.

In order to determine the solids concentration of 0.45 μm filtered final slurry, a portion of the final slurry sample is filtered before the addition of sucrose using a 0.45 μm syringe filter. A volume of the filtered sample is then added to a tared 20 mL scintillation vial and dried at 80° C. in a vacuum oven. The remaining sample of unfiltered final slurry is frozen with sucrose.

Figure 7:
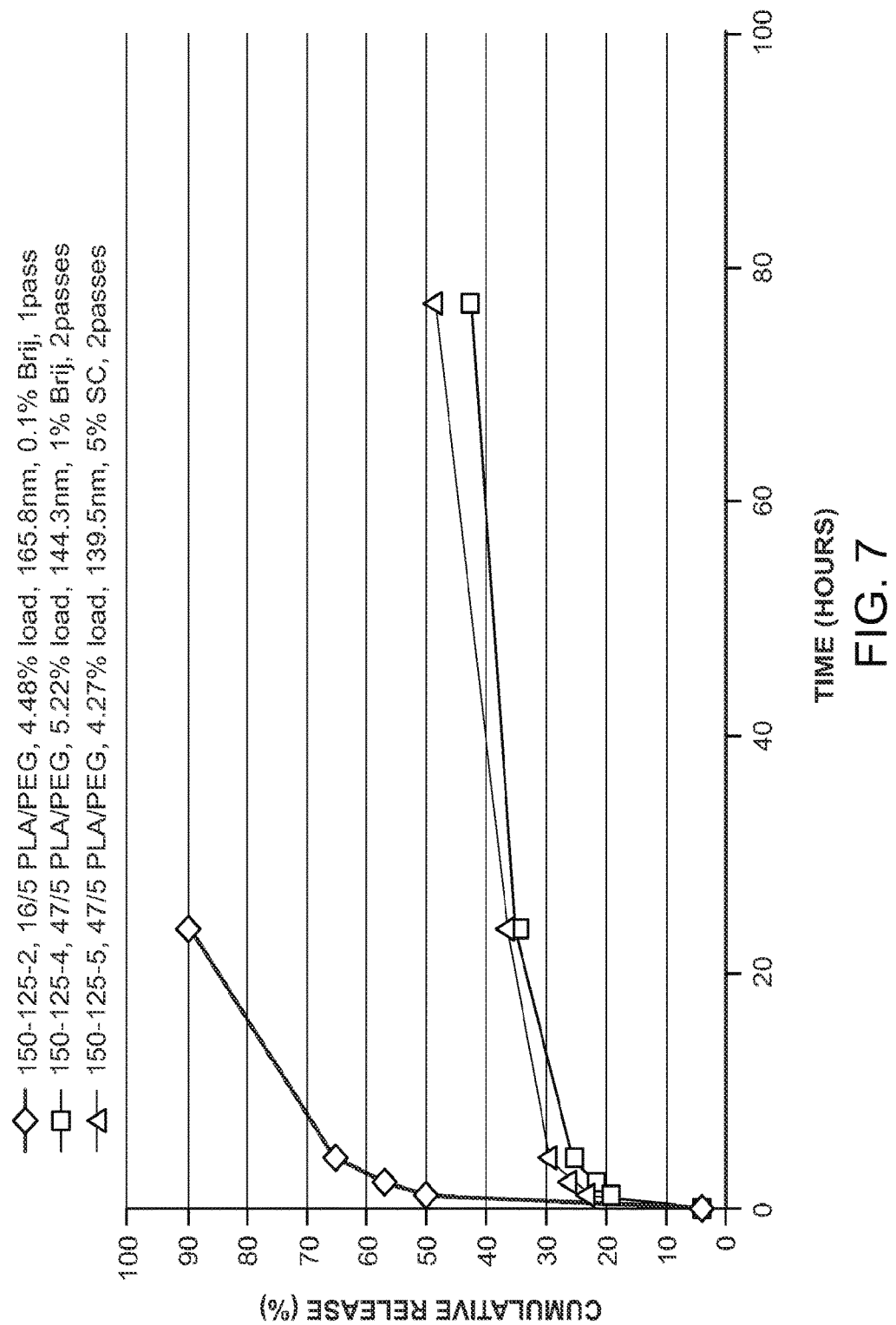
FIG. 7 shows in vitro release data for contemplated docetaxel nanoparticle formulations containing a Brij® 100 excipient.

Table 7 shows the conditions used for formulation nanoparticles. Table 8 shows certain properties of the nanoparticles. Table 9 shows the results of in vitro release of docetaxel from the nanoparticles. FIG. 7 also shows the in vitro release properties of nanoparticles prepared using Brij 100 versus SC.

TABLE 7

Formulation conditions.

| Lot # | PLA-PEG | Drug | Drug theoretical loading | Solid con | Surfactant | pass# @ psi# |
|---|---|---|---|---|---|---|
| 150-125-2 | 16/5 | Docetaxel | 20 | 20% | 0.1% Brij | 1@45 psi |
| 150-125-4 | 47/5 | Docetaxel | 20 | 20% | 1% Brij | 2@45 psi |
| 150-125-5 | 47/5 | Docetaxel | 20 | 20% | 5% SC | 1$^{st}$@60 psi, 2$^{nd}$@45 psi |

TABLE 8

Nanoparticle properties.

| Lot # | Loading % | size (nm) | NP Solids (mg/mL) | Glass transition temperature (Tg, ° C.) |
|---|---|---|---|---|
| 150-125-2 | 4.84% | 165.8 | 6.125 | 37.86 |
| 150-125-4 | 5.22% | 144.3 | 5.1 | 43.21 |
| 150-125-5 | 4.27% | 139.5 | 5.15 | 42.29 |

TABLE 9

In vitro release.

| Time (hours) | Cumulative release (%) | | |
|---|---|---|---|
| | 150-125-2 | 150-125-4 | 150-125-5 |
| 0 | 21.3 | 3.6 | 6.6 |
| 1 | 49.6 | 19.2 | 21.9 |
| 2 | 57.0 | 22.0 | 26.5 |
| 4 | 65.4 | 25.3 | 29.3 |
| 24 | 89.8 | 35.4 | 36.5 |
| 77 | — | 42.33 | 48.34 |

Brij 100 is a non-ionic surfactant, polyoxyethylene (100) stearyl ether, with average $M_n \sim 4,670$. Its HLB value is 18.8. It is composed of two neutral blocks, a lipophilic short chain and a hydrophilic PEG chain. Brij 100 is used in pharmaceuticals as an emulsifier, wetting agent, or oil solubilizer. It is a water-soluble pale yellow solid, and is considered a non-toxic, nonirritant, noncarcinogenic compound, with an LD50 (oral, rat) >16 g/kg.

Two formulations were prepared using Brij 100 as surfactant (150-125-2 and 150-125-4), and one formulation was prepared as a control using sodium cholate as surfactant (150-125-5).

For 16/5 PLA-PEG, 4.84% docetaxel was loaded in nanoparticles using 0.1% of Brij solution as aqueous phase, with particle size of 165.8 nm (150-125-2). For 47/5 PLA-PEG, 5.22% docetaxel was loaded in nanoparticles using 1% Brij (150-125-4). These results are comparable or slightly higher than that of the control batch using sodium cholate as surfactant (150-125-5). The particle sizes of the two lots were similar, 144.3 nm for Brij 100 lot versus 139.5 nm for sodium cholate lot. Collected nanoparticles solid concentrations were also similar: 5.1 mg/mL versus 5.15 mg/mL. Glass transition temperatures of the two lots of nanoparticles are both well above physiological temperature, 37° C., with less than 1° C. difference (43.21° C. versus 42.29° C.).

Docetaxel release from nanoparticles prepared from 16/5 PLA-PEG shows a faster release than that from nanoparticles of 47/5 PLA-PEG, which is controlled mainly by polymer MW. Nanoparticles prepared from 47/5 PLA-PEG and either Brij 100 or sodium cholate as surfactant show similar release profiles, with a minor fluctuation of <±2% difference. Overall, no significant difference was observed for nanoparticles produced using Brij 100 or sodium cholate as surfactant with respect to drug loading, yield, particle size, and in vitro release profiles. Using Brij 100 as a surfactant yielded similar nanoparticles as compared to using sodium cholate as the surfactant. In addition, a much lower Brij 100 concentration (1%) was used in comparison to sodium cholate (5%) indicating that the concentration of Brij could be increased if necessary. Consequently, Brij 100 could be advantageous to use instead of sodium cholate when formulating nanoparticles from high MW PLA-PEG polymers, which benefit from surfactants with higher emulsification capability to produce nanoparticles having smaller diameters.

Further benefits to using PEO-PLA over sodium cholate are (1) non-ionic neutral molecule, which is inert to most compounds, (2) lower concentration than sodium cholate when making nanoparticles under the same conditions, which potentially broadens formulation capability, and (3) more economical pricing at $86.8/1 kg for Brij 100 versus $91.3/100 g for sodium cholate (Sigma).

Example 6

Celecoxib Nanoparticle Formulations Prepared Using a Water-Miscible Organic Solvent Therapeutic nanoparticles were produced using the following formulation:
10% (w/w) theoretical drug;
90% (w/w) Polymer (45/5 PLA-PEG);
% Total Solids=10%;
Solvents: 33-98% 21/79 BA/EA (21/79 BA/EA=21% benzyl alcohol, 79% ethyl acetate (w/w))+DMSO or DMF;

For a 1 gram batch size, 100 mg of drug and 900 mg of 45/5 PLA-PEG were used.

Therapeutic nanoparticles are produced as follows. In order to prepare a drug solution, 100 mg of celecoxib and 990 mg of dimethylsulfoxide were added to a 20 mL glass vial and vortexed until the drug was dissolved. To prepare a polymer solution, 900 mg of PLA-PEG were added to a second 20 mL glass vial along with 8010 mg of benzyl alcohol/ethyl acetate mixture (21 wt. %/79 wt. %, respectively) and the mixture vortexed until the polymer was dissolved. The drug solution and the polymer solution were combined and vortexed prior to formulation of the nanoparticles.

An aqueous solution was prepared containing 0.4% sodium cholate dissolved in a solution of 2 wt. % benzyl alcohol and 4 wt. % ethyl acetate in water. Specifically, to a 1 L bottle was added 4 g sodium cholate and 956 g of DI water and the mixture stirred on a stir plate until dissolved. To this solution was added 20 g of benzyl alcohol and 40 g of ethyl acetate and the mixture stirred on a stir plate until dissolved.

An emulsion was formed by combining the organic phase into the aqueous solution at a ratio of 5:1 (aqueous phase:oil phase). The organic phase was poured into the aqueous solution and homogenized using a hand homogenizer for 10 seconds at room temperature to form a coarse emulsion. The coarse emulsion was subsequently fed through a high pressure homogenizer (110S) by setting the pressure to 25 psi for one pass to form a nanoemulsion.

The nanoemulsion was quenched into cold DI water at <5° C. while stirring on a stir plate. The ratio of Quench to Emulsion was 5:1.

The nanoparticles were concentrated through tangential flow filtration (TFF) followed by diafiltration to remove solvents, unencapsulated drug, and solubilizer. A quenched emulsion was initially concentrated through TFF using a 300 KDa Pall cassette (2 membrane) to an approximately 200 mL volume. This was followed by diafiltration using approximately 20 diavolumes (4 L) of cold DI water. The volume was minimized by adding 100 mL of cold water to the vessel and pumping through the membrane for rinsing. Approximately 50-100 mL of material were collected in a glass vial.

In order to determine the solids concentration of unfiltered final slurry, a 10 mL volume of final slurry was added to a tared 20 mL scintillation vial and dried under vacuum at 80° C. in a vacuum oven. Subsequently, the weight of nanoparticles was determined in the volume of the dried down slurry. Concentrated sucrose (0.111 g/g) is added to the final slurry sample to attain a final concentration of 10% sucrose.

In order to determine the solids concentration of 0.45 µm filtered final slurry, a portion of the final slurry sample is filtered before the addition of sucrose using a 0.45 µm syringe filter. A volume of the filtered sample is then added to a tared 20 mL scintillation vial and dried at 80° C. in a vacuum oven. The remaining sample of unfiltered final slurry is frozen with sucrose.

Figure 8:
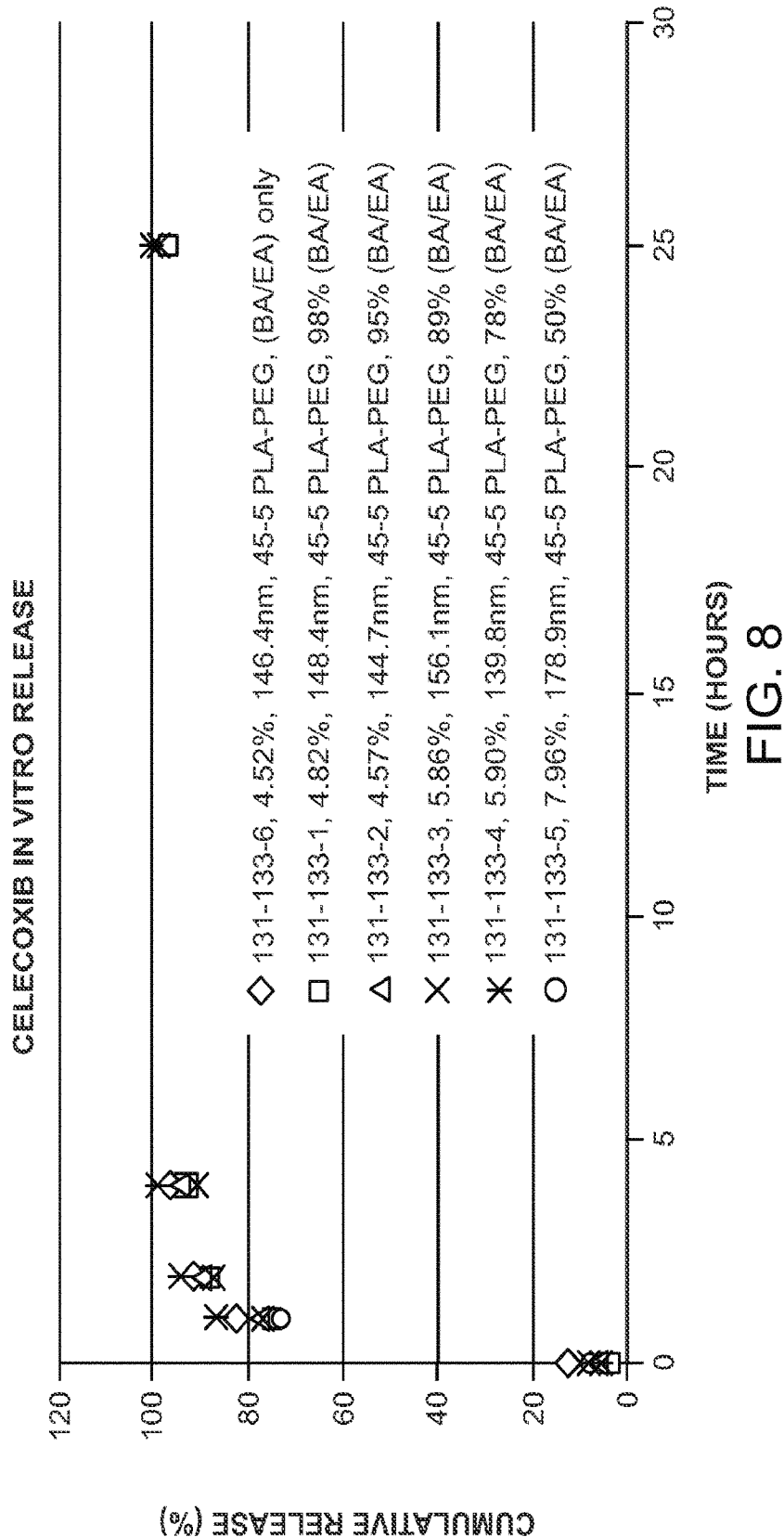
FIG. 8 shows in vitro release data for contemplated docetaxel nanoparticle formulations containing a polyethylene oxide-polylactic acid block copolymer excipient as compared to a control.

Table 10 shows the conditions used for formulation nanoparticles. Table 11 shows certain properties of the nanoparticles. Table 12 shows the results of in vitro release of celecoxib from the nanoparticles. FIG. 8 also shows the in vitro release properties of nanoparticles prepared using DMSO.

TABLE 1

Formulation conditions.

| Organic phase solvent | Lot # | BA/EA (wt. %) | Drug theoretical loading (%) | Solid conc. | % SC, pass# @ psi# |
|---|---|---|---|---|---|
| BA/EA only (control) | 131-133-6 | 100 | 10 | 10% | 0.4%, 1@25 psi |
| Mixture of (BA/EA) and DMSO | 131-133-1 | 98 | 10 | 10% | 0.4%, 1@25 psi |
| | 131-133-2 | 95 | 10 | 10% | 0.4%, 1@25 psi |
| | 131-133-3 | 89 | 10 | 10% | 0.4%, 1@25 psi |
| | 131-133-4 | 78 | 10 | 10% | 0.4%, 1@30 psi |
| | 131-133-5 | 50 | 10 | 10% | 0.4%-0.56%, 5@30 psi-60 psi |

TABLE 1-continued

Formulation conditions.

| Organic phase solvent | Lot # | BA/EA (wt. %) | Drug theoretical loading (%) | Solid conc. | % SC, pass# @ psi# |
|---|---|---|---|---|---|
| Mixture of BA/EA and DMF | 131-150-4 | 98 | 10 | 10% | 0.4%, 1@25 psi |
| | 131-145-5 | 89 | 10 | 10% | 0.4%, 1@25 psi |
| | 131-150-6 | 50 | 10 | 10% | 0.5%, 2@45 psi |
| | 131-150-2 | 33 | 10 | 6.9% | 1%-2%, @45 psi-60 psi |

TABLE 2

Nanoparticle properties.

| Organic phase solvent | Lot # | Drug loading % | Loading efficiency % | size (nm) | NP Solids (mg/mL) | Yield (%) |
|---|---|---|---|---|---|---|
| BA/EA only (control) | 131-133-6 | 4.52 | 45.2 | 146.4 | 7.625 | 65.2 |
| Mixture of (BA/EA) and DMSO | 131-133-1 | 4.82 | 48.2 | 148.4 | 7.775 | 67.5 |
| | 131-133-2 | 4.57 | 45.7 | 144.7 | 6.725 | 58.6 |
| | 131-133-3 | 5.86 | 58.6 | 156.1 | 6.725 | 66.5 |
| | 131-133-4 | 5.9 | 59 | 139.8 | 7.525 | 61.1 |
| | 131-133-5 | 7.96 | 79.6 | 178.9 | 4.125 | 34.8 |
| Mixture of (BA/EA) and DMF | 131-150-4 | 4.52 | 45.2 | 145.6 | 7.275 | 69.3 |
| | 131-145-5 | 5.17 | 51.7 | 139.9 | 8.975 | 66.7 |
| | 131-150-6 | 7.65 | 76.5 | 160.5 | 5.525 | 54.5 |
| | 131-150-2 | 6.63 | 66.3 | 502.7 | 5.275 | 41.8 |

TABLE 3

In vitro release of control batch and batches using (BA/EA) mixture with DMSO.

| Time (hours) | Cumulative release (%) | | | | | |
|---|---|---|---|---|---|---|
| | 131-133-6 | 131-133-1 | 131-133-2 | 131-133-3 | 131-133-4 | 131-133-5 |
| 0 | 6.89 | 4.31 | 4.33 | 6.80 | 7.14 | 12.01 |
| 1 | 82.98 | 74.49 | 83.28 | 81.73 | 87.32 | 79.29 |
| 2 | 92.42 | 88.65 | 91.88 | 87.50 | 95.24 | 89.32 |
| 4 | 96.70 | 93.31 | 94.41 | 90.59 | 96.46 | 93.26 |
| 25 | 99.40 | 96.68 | 98.13 | 96.73 | 100.60 | 98.58 |

Nanoparticle (NP) solids concentration in the range of about 5-8 mg/mL was observed for all formulations, and NP yields were all above 50%, except two batches with lower (BA/EA) content, lot 131-133-5 with 50% (BA/EA) and lot 131-150-2 with 33% (BA/EA).

Particle sizes were well controlled in the range of about 140-160 nm for all batches with BA/EA content ≥50%. When BA/EA content dropped to 33% for lot 131-150-2, significantly larger particles (502.7 nm) were observed, even when using up to 2% sodium cholate and 60 psi pressure.

Drug loadings of all formulations were equal to or higher than the control. These results demonstrate the potential to use these mixtures to improve drug loading. In vitro release profiles from batches using (BA/EA) mixture with DMSO overlay with the release from the control batch, lot 131-133-6. Adding water miscible solvents to the organic phase do not affect in vitro release of nanoparticles.

Overall, by adding water miscible solvents, DMSO or DMF, to organic phase at reasonable amount of up to 50%, decent nanoparticles could be prepared using BIND nanoemulsion method without changing in vitro release of nanoparticles. The value for this modified solvent phase is potentially broadening the range of drugs which could be encapsulated using the nanoemulsion method. Because DMSO and DMF are generally good solvents for most compounds, drugs (insoluble in organic solvents used in the nanoemulsion method, including benzyl alcohol, ethyl acetate, and methylene chloride) may easily be dissolved in DMSO or DMF. When mixing DMSO or DMF with a non-solvent for a drug (e.g., BA, EA or $CH_2Cl_2$), the drug's solubility could be improved generally, which benefits drug encapsulation by increasing theoretical drug loading. Drugs that could not be encapsulated or have demonstrated low encapsulation efficiency previously could be potentially encapsulated using these modified organic phase solvents.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A therapeutic nanoparticle comprising:
   about 0.05 to about 30 weight percent of an excipient selected from the group consisting of a polyanionic polymer and a polycationic polymer;
   about 0.2 to about 35 weight percent of a therapeutic agent;
   1,2-distearoyl-sn-glycero-3-phosphoethanolamine-poly(ethylene)glycol copolymer; and
   about 35 to about 99.75 weight percent of a biocompatible polymer.

2. The therapeutic nanoparticle of claim 1, wherein the excipient is a polyanionic polymer, wherein the polyanionic polymer is a copolymer of methacrylic acid and methyl methacrylate subunits.

3. The therapeutic nanoparticle of claim 2, wherein the ratio of methacrylic acid to methyl methacrylate subunits is between about 1:0.9 to about 1:3.

4. The therapeutic nanoparticle of claim 1, wherein the excipient is a polycationic polymer, wherein the polycationic polymer is: i) a copolymer of alkyl methacrylate and dimethylaminoethylmethacrylate, or ii) a copolymer of dimethylaminoethyl methacrylate, butyl methacrylate, and methyl methacrylate subunits.

5. The therapeutic nanoparticle of claim 4, wherein the ratio of dimethylaminoethyl methacrylate to butyl methacrylate to methyl methacrylate subunits is about 1:2:1.

6. The therapeutic nanoparticle of claim 1, wherein the excipient has a molecular weight of between about 20 kDa and about 60 kDa.

7. The therapeutic nanoparticle of claim 1, wherein the excipient has a molecular weight of between about 100 kDa and about 150 kDa.

8. The therapeutic nanoparticle of claim 1, further comprising about 0.05 to about 35 weight percent cyclodextrin, wherein the cyclodextrin is selected from the group consisting of α-cyclodextrin, β-cyclodextrin, γ-cyclodextrin, and mixtures thereof.

9. The therapeutic nanoparticle of claim 8, comprising about 15 to about 30 weight percent cyclodextrin.

10. The therapeutic nanoparticle of claim 1, wherein the therapeutic agent is a chemotherapeutic agent.

11. The therapeutic nanoparticle of claim 1, wherein the hydrodynamic diameter of the therapeutic nanoparticle is about 60 to about 200 nm.

12. The therapeutic nanoparticle of claim 1, wherein the biocompatible polymer is selected from the group consisting of poly(lactic) acid-poly(ethylene)glycol copolymer and poly(lactic) acid-co-poly(glycolic) acid-poly(ethylene)glycol copolymer.

13. The therapeutic nanoparticle of claim 12, wherein the poly(lactic) acid-poly(ethylene)glycol copolymer has a poly(lactic) acid number average molecular weight fraction of about 0.6 to about 0.95.

14. The therapeutic nanoparticle of claim 1, wherein the therapeutic nanoparticle comprises about 10 to about 25 weight percent poly(ethylene)glycol.

15. The therapeutic nanoparticle of claim 1, wherein the therapeutic nanoparticle comprises about 20 to about 30 weight percent poly(ethylene)glycol.

16. The therapeutic nanoparticle of claim 1, wherein the nanoparticle substantially immediately releases less than about 70% of the therapeutic agent after 0.5 hours when placed in a phosphate buffer solution at 37° C.

17. A pharmaceutically acceptable composition comprising a plurality of therapeutic nanoparticles of claim 1, and a pharmaceutically acceptable excipient.

18. The pharmaceutically acceptable composition of claim 17, further comprising a saccharide and/or cyclodextrin.

19. The pharmaceutically acceptable composition of claim 18, wherein the saccharide is a disaccharide selected from the group consisting of sucrose or trehalose, or a mixture thereof.

20. The pharmaceutically acceptable composition of claim 18, wherein the cyclodextrin is selected from the group consisting of α-cyclodextrin, β-cyclodextrin, γ-cyclodextrin, and mixtures thereof.

* * * * *